US007901900B2

(12) United States Patent
Furusako et al.

(10) Patent No.: US 7,901,900 B2
(45) Date of Patent: Mar. 8, 2011

(54) ASSAY KIT AND ANTIBODY FOR HUMAN LOW MOLECULAR WEIGHT CD14

(75) Inventors: Shoji Furusako, Shizuoka (JP); Kamon Shirakawa, Shizuoka (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 491 days.

(21) Appl. No.: 11/987,746

(22) Filed: Dec. 4, 2007

(65) Prior Publication Data

US 2009/0029396 A1    Jan. 29, 2009

Related U.S. Application Data

(62) Division of application No. 10/534,257, filed as application No. PCT/JP03/14389 on Nov. 12, 2003, now Pat. No. 7,465,547.

(30) Foreign Application Priority Data

Nov. 12, 2002   (JP) .................................. 2002-328866
Sep. 22, 2003   (JP) .................................. 2003-330775

(51) Int. Cl.
*G01N 33/53*   (2006.01)
*C07K 16/18*   (2006.01)

(52) U.S. Cl. ...................... 435/7.94; 435/7.9; 530/387.1; 530/388.1; 530/388.25

(58) Field of Classification Search ........................ None
See application file for complete search history.

(56) References Cited

U.S. PATENT DOCUMENTS

| 4,931,385 | A | * | 6/1990 | Block et al. ................... 435/7.94 |
| 5,766,593 | A | | 6/1998 | Lichenstein et al. |
| 6,916,628 | B1 | | 7/2005 | Furusako et al. |
| 7,326,568 | B2 | * | 2/2008 | Gaertig et al. ................. 435/325 |
| 2004/0141917 | A1 | | 7/2004 | Achen et al. |

FOREIGN PATENT DOCUMENTS

| DE | 286876 A | 10/1983 |
| DE | 286876 A5 | 2/1991 |
| EP | 1213586 A1 | 6/2002 |
| EP | 1 275 713 A1 | 1/2003 |
| EP | 1 275 713 A1 | 1/2003 |
| EP | 1 336 620 A1 | 8/2003 |
| EP | 1 336 620 A1 | 8/2003 |
| EP | 1571160 A1 | 9/2005 |
| WO | WO-96/20956 A1 | 7/1996 |
| WO | WO-01-22085 A1 | 3/2001 |
| WO | WO-01/72993 A1 | 10/2001 |
| WO | WO-02/42333 A1 | 5/2002 |

OTHER PUBLICATIONS

Bufler et al., European Journal of Immunology, Feb. 1995, vol. 25, No. 2, XP-002458844, pp. 604-610.
Majerle et al., European Journal of Physiology 2000, vol. 439, No. 3, XP-002458846 pp. R109-R110.
Stelter et al., European Journal of Biochemistry, vol. 243, No. 1-2, (1997), XP-002458847, pp. 100-109.
Majerle et al., Protein Expression and Purification, vol. 17, No. 1, 1999, pp. 96-104.
Iwaki et al. Biochemical and Biophysical Research Communications, vol. 328, No. 1, (2005), pp. 173-176.
Kim et al.; The Journal of Biological Chemistry, vol. 280, No. 12, pp. 11347-11351 (2005).
Levenson, Clinical Laboratory News 2008, vol. 34, No. 1, AACC (available at aacc.org) pp. 1-8.
Wenisch et al. Clin. Exp. Immunol. 1996, 105: pp. 74-78.
Lien et al. Blood 1998, 92: 2084-2092.
Levenson Clinical Laboratory News 2008, vol. 34, No. 1, [retrieved on Feb. 12, 2008]. Retrieved from the Internet: < URL: http://www.aacc.org/AACC/publications/cln/2008/jan/cover1_0108.htm>   p. 1-8.
Weinisch et al. Clin Exp Immunol 1996, 105:74-78.
Lien et al. Blood 1988, 92:2084-2092.
Manocha, Sanjay et al.; Expert Opin. Investig. Drugs, vol. 11, No. 12, pp. 1795-1812 (2002).
Lederman et al., Molecular Immunology, vol. 28, pp. 1171-1181, (1991).
Li et al., Biochemistry: Proc. Natl. Acad. Sci. USA, vol. 77, No. 6, pp. 3211-3214, (Jun. 1980).
Abaza et al., Journal of Protein Chemistry, vol. 11, No. 5, pp. 433-444, (1992).
Coleman et al., Research in Immunology, vol. 145, No. 1, pp. 33-36, (1994).
Endo et al., The Japanese Association for Infectious Diseases, 52nd East Japan Meeting held Oct. 31, 2003 (English translation).
Endo et al., The Journal of Japanese Association for Acute Medicine, vol. 14, No. 10, p. 602 (Oct. 2003), English translation.
The Official Journal of the Shock Society, Abstract of the 6th World Congress on Trauma, Shock, Inflammation and Sepsis (Mar. 2004).
Endo et al., Journal of the Japanese Society of Intensive Care Medicine, vol. 11, Supplement, p. 244, Jan. 2004, English translation.
The Official Journal of the Critical Care Forum, vol. 8, Supplement 1, pp. S94-S94 (Mar. 2004).
Abstract of the 104th General Assembly of the Japan Surgical Society, Apr. 2004, English translation.
Official Journal of the European Society of Intensive Care Medicine and the European Society of Paediatric & Neonatal Intensive Care, vol. 30, Supplement 1, p. S192, Sep. 2004.
Endo et al., Program and Abstracts of the 10th Conference of the Japan Endotoxin Society, Nov. 15, 2004, English translation.
Journal of Endotoxin Research, vol. 10, No. 5, p. 373, Nov. 2004.
Endo et al., Journal of the Japanese Society of Intensive Care Medicine, vol. 12, Supplement, p. 121, Jan. 2005, English translation.

(Continued)

*Primary Examiner* — Sharon Wen
(74) *Attorney, Agent, or Firm* — Birch, Stewart, Kolasch & Birch, LLP

(57) ABSTRACT

The present invention provides an antibody prepared using a peptide as an antigen, the peptide having 8 to 30 amino acid residues selected from an amino acid sequence at positions 1 to 68 of human high-molecular-weight CD14, or an antibody that binds to a peptide having a specific amino acid sequence at a position among the positions 1 to 68. An assay kit for human low-molecular-weight CD14 using the antibody and an assay method of the present invention, preferably a sandwich method, are able to quantitatively or qualitatively determine human low-molecular-weight CD14 with high sensitivity and specificity in a simple manner, so that they are useful for the diagnosis of a patient suffering from sepsis.

5 Claims, 7 Drawing Sheets

OTHER PUBLICATIONS

Endo et al., The Journal of the Japanese Association for Infectious Diseases, vol. 80, Supplement, p. 271, Mar. 2006, English translation.

Endo et al., Japan Journal of Critical Care for Endotoxemia, vol. 9, No. 1, pp. 46-50, 2005 (English Abstract on p. 50).

Yaegashi et al., Japanese Society of Chemotherapy; pp. 234-238, No. 11 (2005).

Landmann, Regine et al.; The Journal of Infectious Disease, vol. 171, pp. 639-644 (1995).

Stelter, Felix et al.; European Journal of Biochemistry (Germany); vol. 236, pp. 457-464 (1996).

Bazil, Vladimir et al.; European Journal of Immunology (Germany); vol. 16, pp. 1583-1589 (1986).

Schütt, Christine et al.; Allergie und Immunologie (Germany), vol. 34, pp. 17-26 (1988).

Van Voorhis, Wesley C. et al.; Journal of Experimental Medicine (USA), vol. 158, pp. 126-145 (1983).

Bazil, Vladimir et al.; Molecular Immunology (UK), vol. 26, pp. 657-662 (1989).

Grunwald, U. et al.; Journal of Immunological Methods (Holland); vol. 155, pp. 225-232 (1992).

Burgmann, Heinz et al.; Clinical Immunology and Immunopathology (USA), vol. 80, pp. 307-310 (1996).

Shigeatsu Endo et al., Journal of Japanese Association for Acute Medicine, Oct. 15, 2003, vol. 14, No. 10, pp. 602, Op-285.

Yaegashi et al., Japanese Society of Chemotherapy and The Japanese Association for the Infections Diseases, vol. 11, No. 5, (2005), pp. 234-238.

European Search Report dated May 29, 2009 from related European Application No. 05739312.6.

Haziot et al., "The Monocyte Differentiation Antigen, CD14, Is Anchored to the Cell Membrane by a Phosphatidylinositol Linkage," The Journal of Immunology, vol. 141, No. 2, Jul. 15, 1988, pp. 547-552.

Schutt, Christine et al.; Allergie und Immunologie (Germany), vol. 34, pp. 17-26 (1988).

* cited by examiner

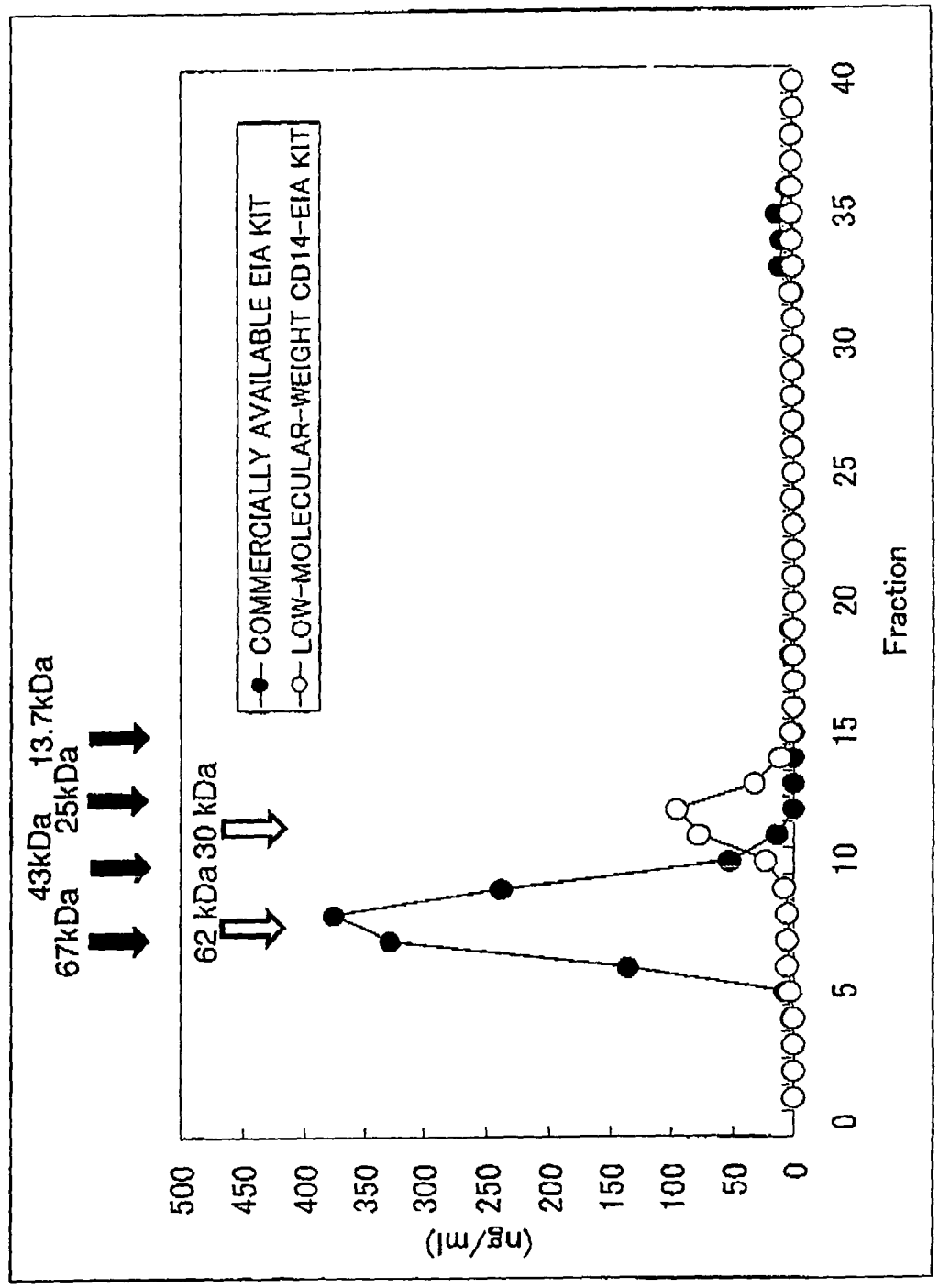

SEQUENCE LISTING

```
<160> NUMBER OF SEQ ID NOS: 19

<210> SEQ ID NO 1
<211> LENGTH: 68
<212> TYPE: PRT
<213> ORGANISM: Human
```

```
<400> SEQUENCE: 1

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
    50                  55                  60

Asp Thr Val Lys
65

<210> SEQ ID NO 2
<211> LENGTH: 16
<212> TYPE: PRT
<213> ORGANISM: Human

<400> SEQUENCE: 2

Arg Val Asp Ala Asp Ala Asp Pro Arg Gln Tyr Ala Asp Thr Val Lys
1               5                   10                  15

<210> SEQ ID NO 3
<211> LENGTH: 17
<212> TYPE: PRT
<213> ORGANISM: Human

<400> SEQUENCE: 3

Thr Thr Pro Glu Pro Cys Glu Leu Asp Asp Glu Asp Phe Arg Cys Val
1               5                   10                  15

Cys

<210> SEQ ID NO 4
<211> LENGTH: 19
<212> TYPE: PRT
<213> ORGANISM: Human

<400> SEQUENCE: 4

Arg Cys Val Cys Asn Phe Ser Glu Pro Gln Pro Asp Trp Ser Glu Ala
1               5                   10                  15

Phe Gln Cys

<210> SEQ ID NO 5
<211> LENGTH: 356
<212> TYPE: PRT
<213> ORGANISM: Human

<400> SEQUENCE: 5

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95
```

```
Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
                180                 185                 190

Leu Met Ala Ala Leu Cys Pro His Lys Phe Pro Ala Ile Gln Asn Leu
            195                 200                 205

Ala Leu Arg Asn Thr Gly Ile Glu Thr Pro Thr Gly Val Cys Ala Ala
        210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
                260                 265                 270

Pro Lys Gly Leu Pro Ala Lys Leu Arg Val Leu Asp Leu Ser Cys Asn
            275                 280                 285

Arg Leu Asn Arg Ala Pro Gln Pro Asp Glu Leu Pro Glu Val Asp Asn
        290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
                340                 345                 350

Arg Gly Phe Ala
        355

<210> SEQ ID NO 6
<211> LENGTH: 8
<212> TYPE: PRT
<213> ORGANISM: Human

<400> SEQUENCE: 6

Arg Val Asp Ala Asp Ala Asp Pro
1               5

<210> SEQ ID NO 7
<211> LENGTH: 8
<212> TYPE: PRT
<213> ORGANISM: Human

<400> SEQUENCE: 7

Val Asp Ala Asp Ala Asp Pro Arg
1               5

<210> SEQ ID NO 8
<211> LENGTH: 8
<212> TYPE: PRT
<213> ORGANISM: Human

<400> SEQUENCE: 8
```

Asp Ala Asp Ala Asp Pro Arg Gln
1               5

<210> SEQ ID NO 9
<211> LENGTH: 8
<212> TYPE: PRT
<213> ORGANISM: Human

<400> SEQUENCE: 9

Ala Asp Ala Asp Pro Arg Gln Tyr
1               5

<210> SEQ ID NO 10
<211> LENGTH: 8
<212> TYPE: PRT
<213> ORGANISM: Human

<400> SEQUENCE: 10

Asp Ala Asp Pro Arg Gln Tyr Ala
1               5

<210> SEQ ID NO 11
<211> LENGTH: 8
<212> TYPE: PRT
<213> ORGANISM: Human

<400> SEQUENCE: 11

Ala Asp Pro Arg Gln Tyr Ala Asp
1               5

<210> SEQ ID NO 12
<211> LENGTH: 8
<212> TYPE: PRT
<213> ORGANISM: Human

<400> SEQUENCE: 12

Asp Pro Arg Gln Tyr Ala Asp Thr
1               5

<210> SEQ ID NO 13
<211> LENGTH: 8
<212> TYPE: PRT
<213> ORGANISM: Human

<400> SEQUENCE: 13

Pro Arg Gln Tyr Ala Asp Thr Val
1               5

<210> SEQ ID NO 14
<211> LENGTH: 8
<212> TYPE: PRT
<213> ORGANISM: Human

<400> SEQUENCE: 14

Arg Gln Tyr Ala Asp Thr Val Lys
1               5

<210> SEQ ID NO 15
<211> LENGTH: 13
<212> TYPE: DNA
<213> ORGANISM: Artificial Sequence
<220> FEATURE:
<223> OTHER INFORMATION: Oligomer:8 linkS

<400> SEQUENCE: 15

```
agcttaggaa ttt                                                              13

<210> SEQ ID NO 16
<211> LENGTH: 13
<212> TYPE: DNA
<213> ORGANISM: Artificial Sequence
<220> FEATURE:
<223> OTHER INFORMATION: Oligomer:8 linkA

<400> SEQUENCE: 16
ctagaaattc cta                                                              13

<210> SEQ ID NO 17
<211> LENGTH: 26
<212> TYPE: DNA
<213> ORGANISM: Artificial Sequence
<220> FEATURE:
<223> OTHER INFORMATION: Sense Primer

<400> SEQUENCE: 17
acatctagat gaccacgcca gaacct                                                26

<210> SEQ ID NO 18
<211> LENGTH: 30
<212> TYPE: DNA
<213> ORGANISM: Artificial Sequence
<220> FEATURE:
<223> OTHER INFORMATION: Antisense Primer

<400> SEQUENCE: 18
tttggatcct tactagagat cgagcaatct                                            30

<210> SEQ ID NO 19
<211> LENGTH: 14
<212> TYPE: PRT
<213> ORGANISM: Artificial Sequence
<220> FEATURE:
<223> OTHER INFORMATION: Negative Control Peptide

<400> SEQUENCE: 19

Cys Glu Gly Asn Gly Asn Asn Phe Glu Ser Arg Glu Ala Cys
1               5                   10
```

ASSAY KIT AND ANTIBODY FOR HUMAN LOW MOLECULAR WEIGHT CD14

This application is a Divisional of application Ser. No. 10/534,257 filed on May 10, 2005 now U.S. Pat 7,465,547, and for which priority is claimed under 35 U.S.C. §120 and which is a National Stage Application based on International Application No. PCT/JP03/14389 filed on Nov. 12, 2003; and this application claims priority of Application No. 2002-328866 filed in Japan on Nov. 12, 2002 and Application No. 2003-330775 filed in Japan on Sep. 22, 2003 under 35 U.S.C. §119; the entire contents of all are hereby incorporated by reference.

TECHNICAL FIELD

The present invention relates to an antibody prepared using a peptide as an antigen, the peptide having 8 to 30 amino acid residues selected from specific amino acid sequences for human high molecular weight CD14. Furthermore, the present invention relates to an antibody that binds to a peptide having a specific amino acid sequence in amino acid sequences for human high molecular weight CD14.

In addition, the present invention relates to an assay kit for human low-molecular-weight CD14 and a method of measuring the same. Furthermore, the present invention relates to a novel diagnostic method for sepsis in which human low-molecular-weight CD14 is determined directly. Furthermore, the present invention relates to a peptide useful for the preparation of the above antibody and a method of preparing the antibody.

BACKGROUND ART

A CD14 molecule was named as a protein identified by a family of antibodies that recognize glycoproteins ex pressed on the membrane surface of monocytes in Third Leukocyte Typing Conference, 1986. In 1990, Wright et al. elucidated that the CD14 molecule is a receptor for LPS, endotoxin ("Science", vol. 249, p. 1431-1433, 1990). The CD14 molecule is a glycoprotein having a molecular weight of 53-55 kDa, and analyses on cDNA revealed that 1.4 kb mRNA has coding sequence of 356 amino ("Nucleic Acids Research" (U.K.), vol. 16, p. 4173, 1988).

It was reported that human CD14 molecules include soluble CD14 molecules in addition to membrane-bound CD14 molecules and blood contains soluble CD14 molecules having different molecular weights ("European Journal of Immunology" (Germany), vol. 23, p. 2144-2151, 1993). In addition, Landmann et al. conducted Western blot analyses on soluble CD14 in serum of patients suffering from sepsis and reported that soluble CD14 of about 55 kDa is at high levels in non-survival sepsis patients and patients with paroxysmal nocturnal hemoglobinuria (PNH) and that in normal sera, this molecule was not detected but soluble CD14 of 49-kDa, a slightly lower molecular weight than the former, was detected ("The Journal of Infectious Disease", vol. 171, p. 639-644, 1995).

Stelter reported that the difference in sugar chains is involved in those subtypes having different molecular weights and two soluble CD14 subtypes having different molecular weights are found in blood even after removal of N- and O-linked sugar chains ("European Journal of Biochemistry" (Germany), vol. 236, p. 457-464, 1996). In addition, Bufler et al. conducted the C-terminal analysis on soluble CD14 and reported that a GPI group binds to a serine residue at position 327 of soluble CD14 and that a soluble CD14 molecule having a molecular weight of about 56 kDa is one of the molecular species from which GPI is not anchored ("European Journal of Immunology" (Germany), vol. 25, p. 604-610, 1995).

Antibodies against CD14 molecules include many anti-CD14 antibodies, which have been prepared and used in identification of CD14 proteins, such as MEM-18 prepared by Bazil et al. ("European Journal of Immunology" (Germany), vol. 16, p. 1583-1589, 1986), RoMo-1 prepared by Shutt et al. ("Allergie und Immunologie" (Germany), vol. 34, p. 17-26, 1988), and 3C10 prepared by Steinman et al. ("Journal of Experimental Medicine" (U.S.A.), vol. 158, p. 126-145, 1983).

Furthermore, soluble-CD14 assay systems using those antibodies have been reported by Shutt et al. (DE-286876-A), Bazil et al. ("Molecular Immunology" (U.K.), vol. 26, p. 657-662, 1989), and Grunwald et al. ("Journal of Immunological Methods" (Holland), vol. 155, p. 225-232, 1992), allowing the assay of soluble CD14 in human body fluid.

Furthermore, soluble CD14-ELISA kits have been released on the market from IBL-Hanburg, Medgenix, and R & D Systems, and the assay of soluble CD14 has been performed for many diseases such as sepsis ("Clinical Immunology And Immunopathology" (U.S.A.), vol. 80, p. 307-310, 1996; and "Rinshokensa", vol. 38, p. 341-344, 1994).

However, it was found that soluble CD14 is not a sepsis-specific marker because of increases in levels of soluble CD14 molecules of about 55 kDa and 49 kDa (from report to report, the molecular weights are different and not limited to about 55 kDa and 49 ka, and the same will be applied in the following description) depending on the degree of proceeding of diseases even in diseases except sepsis ("Infection and Immunity" (U.S.A.), vol. 67, p. 417-420, 1999; "Clinical and Experimental Immunology" (U.K.), vol. 120, p. 483-487, 2000; and "Clinical Experimental Immunology" (U.K.), vol. 96, p. 15-19, 1994). Furthermore, the soluble CD14 was expected to be a marker for the severity of sepsis. However, the soluble CD14 has not been provided as a diagnostic product for sepsis because of no correlation with septic shock ("Pediatric allergy and immunology) (Denmark), vol. 8, p. 194-199, 1997) and also no correlation with systemic inflammatory response syndrome (SIRS) ("European Journal of Clinical Investigation" (U.K.), vol. 28, p. 672-678, 1998).

The inventors of the present invention have found out the presence of a soluble CD14 molecule with a low molecular weight of about 36 kDa in blood in addition to others such as two kinds of soluble CD14 molecules described above of about 55 kDa and 49 kDa reported by Landmann et al. (high molecular weight CD14 (from report to report, the molecular weights are different and not limited to about 55 kDa and 49 ka, and the same will be applied in the following description). The inventors of the present invention have also found out the presence of a small amount of the low-molecular-weight CD14 in normal individuals and of an increased amount of the low-molecular-weight CD14 in patients suffering from sepsis. Consequently, the inventors of the present invention have validated the clinical efficacy of the assay on a soluble low-molecular-weight CD14. However, the anti-CD14 antibodies known in the art are those that recognize a high-molecular-weight soluble CD14 protein or those recognize both high- and low-molecular-weight soluble CD14 proteins. Thus, no antibody that recognizes only a low-molecular-weight CD14 has been known in the art. Besides, the amino acid sequence of the low-molecular-weight CD14 protein has been considered to be identical with a part of the amino acid sequence of the high-molecular-weight soluble CD14 protein, so that the preparation of an antibody as described above and a direct immunological assay on the low-molecular-weight CD14 using the antibody have been considered to be difficult. Therefore, as an assay for the soluble low-molecular-weight CD14, there is a proposal in which the level of low-molecular-weight CD14 in blood is indirectly obtained by subtracting the level of high-molecular-weight CD14 in blood from the total level of the soluble CD14 in blood (International publication WO 01/22085).

DISCLOSURE OF THE INVENTION

Under such circumstances, an assay for qualitatively or quantitatively determining human low-molecular-weight CD14 with high sensitivity and specificity in a convenient manner, the assay allowing direct determination of the human low-molecular-weight CD14 and being useful for the diagnosis of a patient suffering from sepsis, and an assay kit for the assay have been desired. Furthermore, an antibody against the human low-molecular-weight CD14 useful for the assay has been desired.

The inventors of the present invention have invented, as a result of the extensive study, an antibody prepared using a peptide as an antigen, the peptide having 8 to 30 amino acid residues selected from amino acid sequences at positions 1 to 68 of human high-molecular-weight CD14 as an antibody which can be used for qualitatively or quantitatively determining human low-molecular-weight CD14 with high sensitivity and specificity in a convenient manner. In addition, the inventors of the present invention have invented an antibody that binds to a peptide having a specific amino acid sequence in the amino acid sequence for the human high-molecular-weight CD14.

Furthermore, the inventors of the present invention have invented an assay for specifically determining human low-molecular-weight CD14 and an assay kit for human low-molecular-weight CD14. Still furthermore, the inventors of the present invention have invented a novel diagnostic method for sepsis in which human low-molecular-weight CD14 is determined directly. Besides, the inventors of the present invention have invented a peptide useful for the preparation of the above antibody and a method of preparing the above antibody.

In other words, the present invention provides the following novel antibodies and an assay kit for human low-molecular-weight CD14.

(1) Antibodies as described in the following (1-1) to (1-5):
(1-1) An antibody prepared using a peptide as an antigen, the peptide having consecutive 8 to 30 amino acid residues selected from an amino acid sequence described in SEQ ID NO: 1.
(1-2) An antibody prepared using a peptide as an antigen, the peptide having consecutive 8 to 20 amino acid residues selected from an amino acid sequence described in SEQ ID NO: 1.
(1-3) An antibody prepared using a peptide as an antigen, the peptide having consecutive 8 to 16 amino acid residues selected from amino acid sequences at positions 53 to 68 in the amino acid sequence described in SEQ ID: 1.
(1-4) An antibody prepared using a peptide as an antigen, the peptide having amino acid residues described in any one of SEQ ID NOS: 2 to 4.
(1-5) An antibody prepared using a peptide as an antigen, the peptide having 16 amino acid residues described in SEQ ID NO: 2.
(2) Antibodies as described in the following (2-1) and (2-2):
(2-1) An antibody that binds to a peptide having amino acid residues described in any one of SEQ ID NOS: 2 to 4.
(2-2) An antibody that binds to a peptide having 16 amino acid residues described in SEQ ID NO: 2.
(3) Assay kits for human low-molecular-weight CD14, represented in the following (3-1) to (3-22):
(3-1) An assay kit for human low-molecular-weight CD14 for directly assaying human low-molecular-weight CD14 in a specimen without detecting human high-molecular-weight CD14, comprising an antibody that binds to at least one of the human low-molecular-weight CD14 or a fragment thereof.
(3-2) The assay kit for human low-molecular-weight CD14 of (3-1), wherein the antibody that binds to the human low-molecular-weight CD14 or the fragment thereof is the antibody described in any one of the above (1-1) to (1-5), (2-1), or (2-2), or a fragment thereof.
(3-3) The assay kit for human low-molecular-weight CD14 of (3-1), wherein the antibody that binds to the human low-molecular-weight CD14 or the fragment thereof is the antibody described in any one of the above (1-4), (1-5), (2-1), or (2-2), or a fragment thereof.
(3-4) The assay kit for human low-molecular-weight CD14 of (3-1), wherein the antibody that binds to the human low-molecular-weight CD14 or the fragment thereof is the antibody described in any one of the above (1-5) or (2-2), or a fragment thereof.
(3-5) The assay kit for human low-molecular-weight CD14 of any one of (3-1) to (3-4), wherein the human low-molecular-weight CD14 is assayed by a sandwich immunoassay method.
(3-6) The assay kit for human low-molecular-weight CD14 of (3-5), further comprising a second binding substance that binds to the human low-molecular-weight CD14.
(3-7) The assay kit for human low-molecular-weight CD14 of (3-6), wherein the second binding substance is an antibody that binds to the human low-molecular-weight CD14 or a fragment thereof.
(3-8) The assay kit for human low-molecular-weight CD14 of (3-6), wherein the second binding substance is a monoclonal antibody that binds to the human low-molecular-weight CD14.
(3-9) The assay kit of (3-6), wherein the second binding substance is an antibody that binds to any one region of: amino acid residues at positions 1 to 52 of human high-molecular-weight CD14; a fragment thereof; an antibody that competes with or shows cross-reactivity with an antibody that binds to any one region of amino acid residues at positions 1 to 52 of the human high-molecular-weight CD14: or a fragment thereof.
(3-10) The assay kit of (3-6), wherein the second biding substance is: an antibody that binds to any one of amino acid residues at positions 17 to 26 of human high-molecular-weight CD14; a fragment thereof; an antibody that competes with or shows cross-reactivity with an antibody that binds to any one of amino acid residues at positions 17 to 26 of the human high-molecular-weight CD14; or the fragment thereof.
(3-11) The assay kit for human low-molecular-weight CD14 of any one of (3-6) to (3-10), wherein the antibody described in any one of the above (1-1) to (1-5), (2-1), or (2-2), or a fragment thereof is binding to an insoluble carrier.
(3-12) The assay kit for human low-molecular-weight CD14 of any one of (3-6) to (3-10), wherein the second binding substance is binding to an insoluble carrier.
(3-13) The assay kit for human low-molecular-weight CD14 of any one of (3-6) to (3-10), wherein the antibody described in any one of the above (1-1) to (1-5), (2-1), or (2-2), or a fragment thereof is labeled.

(3-14) The assay kit for human low-molecular-weight CD14 of any one of (3-6) to (3-11), wherein the second binding substance is labeled.

(3-15) The assay kit for human low-molecular-weight CD14 of any one of (3-6) to (3-14), further comprising: a second specific binding substance and a partner of the second specific binding substance, wherein the second specific binding substance and the partner thereof form second specific binding together.

(3-16) The assay kit for human low-molecular-weight CD14 of (3-15), wherein the second specific binding substance or the partner thereof is binding to an insoluble carrier.

(3-17) The assay kit for human low-molecular-weight CD14 of (3-15), wherein the second specific binding substance or the partner thereof is labeled.

(3-18) The assay kit for human low-molecular-weight CD14 of any one of (3-5) to (3-12), (3-15), and (3-16), further comprising a labeled human low-molecular-weight CD14 or a labeled human low-molecular-weight CD14 analogue, wherein the assay is performed by a sandwich immunoassay based on a competition method.

(3-19) The assay kit for human low-molecular-weight CD14 of any one of (3-5) to (3-18), wherein the label is at least one of an enzyme, a dyestuff, a gold colloid, a colored latex, a chemiluminescent substance, a fluorescent substance, and an isotope.

(3-20) The assay kit for human low-molecular-weight CD14 of any one of (3-5) to (3-19), wherein the sandwich immunoassay method is an assay method utilizing immunochromatography.

(3-21) The assay kit for human low-molecular-weight CD14 of any one of (3-5) to (3-19), wherein the sandwich immunoassay method is an assay method utilizing a flow-through method.

(3-22) The assay kit for human low-molecular-weight CD14 of (3-1), wherein the assay is performed by an agglutination method, a direct solid-phase method, or a competition method.

Furthermore, the following assay for human low-molecular-weight CD14, novel diagnostic method for sepsis, peptide, and method of preparing an antibody are provided:

(4) Assays for human low-molecular-weight CD14 as described in the following (4-1) to (4-3).

(4-1) An assay method for human low-molecular-weight CD14, which is for directly assaying human low-molecular-weight CD14 in a specimen using an antibody that binds to at least one of the human low-molecular-weight CD14 in order to detect the human low-molecular-weight CD14 without detecting human high-molecular-weight CD14.

(4-2) The assay method for human low-molecular-weight CD14 of (4-1), wherein the antibody that binds to the human low-molecular-weight CD14 is the antibody described in any one of the above (1-1) to (1-5), (2-1), or (2-2), or a fragment thereof.

(4-3) The assay for human low-molecular-weight CD14 of (4-2), wherein the human low-molecular-weight CD14 is determined by a sandwich immunoassay.

(5) A diagnostic method for sepsis, which is for directly assaying human low-molecular-weight CD14.

(6) A peptide having amino acid residues described in any one of SEQ ID NOS: 2 to 4.

(7) The methods of preparing antibodies as described in the following (7-1) and (7-2).

(7-1) A method of preparing the antibody of any one of the above (1-1) to (1-5), (2-1), and (2-2), wherein a peptide having consecutive 8 to 30 amino acid residues selected from the amino acid sequence described in SEQ ID NO: 1, or a peptide having amino acid residues described in any one of SEQ ID NOS: 2 to 4 is used as an antigen.

(7-2) A method of preparing an antibody of any one of (1-4), (1-5), (2-1), and (2-2) wherein a peptide having amino acid residues described in any one of SEQ ID NOS: 2 to 4 is used an antigen.

The antibody of the present invention can be used in the assay kit for human low-molecular-weight CD14 of the present invention, and the kit allows qualitative or quantitative measurement of human low-molecular-weight CD14 with high sensitivity and specificity in a convenient manner and is useful for diagnosis of a patient suffering from sepsis.

BRIEF DESCRIPTION OF THE DRAWINGS

FIG. 7 is a diagram showing the results obtained by analyzing the low-molecular-weight CD14 protein and the high-molecular-weight CD14 protein in the sera of patients suffering from sepsis by using the EIA kit for low-molecular-weight CD14 and the commercially-available CD14-EIA kit (IBL-Hamburg), respectively, with gel filtration chromatography, in which black arrows on the upper side of the figure respectively indicate the positions of markers used for calibration, i.e., from the left side, BSA, ovalbumin, chymotrypsinogen-A, and ribonuclease-A.

BEST MODE FOR CARRYING OUT THE INVENTION

Figure 1:
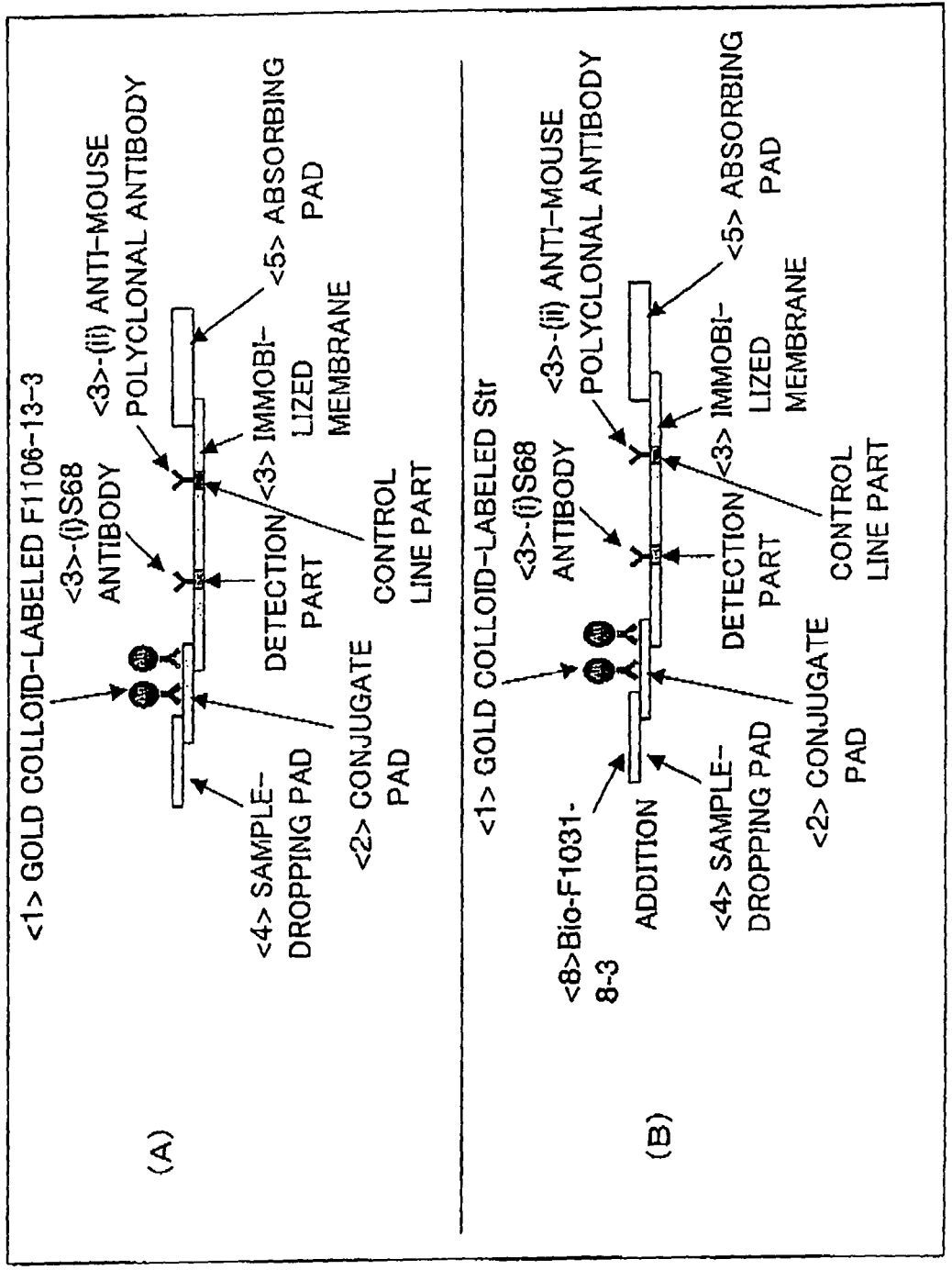
FIG. 1 is a schematic diagram of an immunochromatography kit using an S68-peptide polyclonal antibody, in which part (A) is a schematic diagram of immunochromatographic assay using a gold-colloid-labeled F1031-8-3 as a labeled antibody and part (B) is a schematic diagram of an immunochromatography kit using biotin and streptavidin as second binding substances.

Hereinafter, the present invention will be described in more detail.

Major soluble CD14 molecules in human blood include soluble CD14 molecules of about 55 kDa and about 49 kDa (hereinafter, "human" may be omitted and they may be described as high-molecular-weight CD14 molecules) described in the report by Landmann et al. described in Background Art. It is confirmed that those high-molecular-weight CD14 molecules bind to an F1025-3-1 antibody (see WO 01/22085).

The antibody, F1025-3-1, was deposited on Mar. 30, 1999 under Accession No. FERM BP-7296 with The National Institute of Advanced Industrial Science and Technology (Independent Administrative Institute), International Patent Organism Depositary (IPOD)(Chuo-dairoku, 1-1, Higashi 1-chome, Tsukuba-shi, Ibaraki-ken, Japan).

On the other hand, it is also found that there is a CD14 fragment which does not bind to the F1025-3-1 antibody, in other words, the low-molecular-weight CD14 which has lower molecular-weight is present other than the high-molecular-weight CD14. An increase in level of the low-molecular-weight CD14 in blood with respect to a specific disease is also shown (see WO 01/22085).

Hereinafter, a description will be given of the human low-molecular-weight CD14 (hereinafter, "human" may be omitted and it may be described as low-molecular-weight CD14) provided as an analyte of the assay in the present invention.

The human low-molecular-weight CD14 provided as an analyte of the assay in the present invention has at least three characteristic features as follows:

(1) no binding to an F1025-3-1 antibody;
(2) specific binding to an antibody prepared using a peptide as an antigen, the peptide having 16 amino acid residues described in SEQ ID NO: 2; and
(3) showing a peak in the molecular weight range of 25 to 45 kDa on gel filtration chromatography.

The characteristic feature (1) described above allows the human low-molecular-weight CD14 provided as an analyte of the assay in the present invention to be recognized as a molecule different from the high-molecular-weight CD14 described above. The F1025-3-1 antibody described in the characteristic feature (1) is an antibody prepared using a peptide as an antigen, the peptide having the amino acid sequences at positions 316 to 328 of the full-length human CD14 described in SEQ ID NO: 5. Thus, because of no binding to the F1025-3-1 antibody, it is conceivable that the sequences at positions 316 and later of the full-length human CD14 described in SEQ ID NO: 5 are not existent in the human low-molecular-weight CD14.

The peptide having 16 amino acids described in SEQ ID NO: 2 described in the above characteristic feature (2) corresponds to 16 amino acid residues at positions 53 to 68 of the human CD14 described in SEQ ID NO: 5. Among human proteins, except human CD14, other proteins that contain the sequence of SEQ ID NO: 2 have not been known up to now, so that the sequence may be a sequence specific to the human CD14. This fact confirms that the peptide provided as an analyte of the assay in the present invention can be one kind of human CD14.

As the characteristic feature (2') instead of the characteristic feature (2), furthermore, human low-molecular-weight CD14 as an analyte of the assay in the present invention may be characterized by biding to an antibody that binds to a peptide having 16 amino acid residues described in SEQ ID: 2.

From the above characteristic feature (3), the human low-molecular-weight CD14 as an analyte of the assay in the present invention shows the peak of elution in the molecular weight range of 25 to 45 kDa by gel filtration chromatography. In general, a molecular-weight analysis with gel filtration chromatography cause variations in the results of the assay depending on the experimental conditions including a resin used for chromatography, the dimensions of a column, and the molecular weight of a marker used. The human low-molecular-weight CD14 as an analyte of the assay in the present invention is characterized in that it can be distinguished from human high-molecular-weight CD14 in gel filtration chromatography and can be eluted at lower molecular weights.

The human low-molecular-weight CD14 having characteristic features, which can be explained by the above (1) to (3), is provided as an analyte of the assay in the present invention. Further preferable characteristic features of the human low-molecular-weight CD14 as an analyte of the assay in the present invention will be described below.

(4) Specific Binding to an Anti-Human CD14 Polyclonal Antibody.

The human low-molecular-weight CD14 as an analyte of the assay in the present invention specifically binds to a polyclonal antibody using the full-length human CD14 or recombinant full-length human CD14 as an antigen. Examples of anti-human CD14 polyclonal antibodies include: antisera having increased antibody titers obtained by immunizing mice with CD14 proteins in human blood as described later in Example 3-(2)-[2]; and specific antibodies included therein.

Furthermore, the human low-molecular-weight CD14 is characterized by binding to a specific anti-CD14 monoclonal antibody. For example, the human low-molecular-weight CD14 is particularly characterized in that it binds to an anti-CD14 monoclonal antibody recognizing an amino acid sequence at positions 17 to 26 of the full-length human CD14 described in SEQ ID NO: 5 or to an anti-CD14 monoclonal antibody that competes with the antibody. Concrete examples of such an antibody include an F1031-8-3 antibody described below prepared using CD14 in human serum as an antigen and an F1106-13-3 antibody described below prepared using recombinant human CD14 as an antigen.

On the other hand, the human low-molecular-weight CD14 is further characterized as follows. The human low-molecular-weight CD14 is characterized in that it may bind to: one of an anti-CD14 monoclonal antibody that recognizes an amino acid sequence at positions 17 to 26 of the full-length human CD14 described in SEQ ID NO: 5 and an anti-CD14 monoclonal antibody that competes with the antibody; and an antibody prepared using a peptide as an antigen, the peptide having 16 amino acid residues described in SEQ ID NO: 2, as described in the above characteristic feature (2) concurrently at two positions. For example, the human low-molecular-weight CD14 is characterized in that it may be assayed by a sandwich method using a combination of these two antibodies.

The inventors of the present invention have found that the human low-molecular-weight CD14 explained in the above description is a soluble protein in human blood and exists more in blood of patients suffering from sepsis compared with normal individuals and that the protein can be directly assayed using a specific antibody. By the way, in WO 01/22085 described above, a protein having a molecular weight of 36 kDa is exemplified as one of molecular species of the low-molecular-weight CD14 as an analyte of the assay.

By the way, the "soluble CD14" described in the present specification means a protein existed in human plasma and is used in contrast with the "membrane-bound CD14" which is attached on a cell membrane but not found in human plasma.

The "antibody prepared using a peptide as an antigen" used in the present invention means an antibody in which a peptide used as an "antigen" is provided as an epitope or a part of an epitope. In addition, it is an antibody that shows an ability of binding to a peptide used as an "antigen" of the "antibody prepared using a peptide as an antigen". The examples of the "antibody prepared using a peptide as an antigen" include antibodies that represent the properties described above even though the antibodies are prepared using peptides as their immunogens with addition of carriers or carrier proteins or other amino acid residues for providing the respective peptides as "antigens" with immunogenicity.

According to a first aspect of the present invention, there is provided an antibody prepared using a peptide as an antigen, the peptide having consecutive 8 to 30 amino acid residues selected from the amino acid sequence described in SEQ ID: 1.

An antibody according to the first aspect of the present invention is prepared using a peptide as an antigen, the peptide having consecutive 8 to 30 amino acid residues selected from the amino acid sequence described in SEQ ID: 1.

The number of amino acid residues is not specifically limited as far as it is an antibody prepared using a peptide as an antigen, the peptide having consecutive 8 to 30 amino acid residues selected from the amino acid sequence described in SEQ ID NO: 1. It is an antibody prepared using a peptide as an antigen, the peptide having preferably 10 or more consecutive amino acids, more preferably 12 or more consecutive amino acids, particularly preferably 16 consecutive amino acids. In addition, it is an antibody prepared using a peptide as an antigen, the peptide having preferably 25 or less, more preferably 20 or less amino acids.

Furthermore, it may be any one region at positions 1 to 68 in the amino acid sequence described in SEQ ID NO: 1 and is not particularly limited. However, preferable is an antibody prepared using a peptide as an antigen, the peptide having consecutive 8 to 16 amino acid residues selected from the amino acid sequences at positions 53 to 68 in the amino acid sequence described in SEQ ID NO: 1. In addition, antibodies prepared using peptides as antigens, the peptide having amino acid residues described in SEQ ID NO: 2-4, respectively, are preferable. SEQ ID NO: 5 describes the amino acid sequence of a full-length human CD14. The amino acid sequence described in SEQ ID NO: 1 corresponds to positions 1 to 68 of the amino acid sequence described in SEQ ID: 5. Furthermore, the amino acid sequences described in SEQ ID NOS: 2, 3, and 4 correspond to positions 53 to 68 (16 amino acid residues), 1 to 17 (17 amino acid residues), and 14 to 32 (19 amino acid residues) of the amino acid sequence described in SEQ ID NO: 5, respectively. That is, each of the amino acid residues described in SEQ ID NOS: 2 to 4 is consecutive amino acid residues included in the amino acid sequence described in SEQ ID NO: 1.

More preferably, it is an antibody prepared using a peptide as an antigen, the peptide having 16 amino acid residues described in SEQ ID NO: 2.

The characteristic feature of the antibody according to the first aspect of the present invention is to bind to human low-molecular-weight CD14. This feature allows the antibody to be used in a kit according to a fourth aspect of the present invention or an assay according to a fifth aspect of the present invention.

Furthermore, the molecular weight of the human low-molecular-weight CD14 is different from that of the high-molecular-weight CD14, and also the amino acid sequence of the former is shorter than that of the latter. For this reason, the conformation of the low-molecular-weight CD14 in blood is different from that of the high-molecular-weight CD14, so that their reactivity with the antibody may be different from each other. Thus, it is conceivable that the antibody according to the first aspect of the present invention strongly binds to the low-molecular-weight CD14.

According to a second aspect of the present invention, there is provided an antibody that binds to a peptide having amino acid residues described in any one of SEQ ID NOS: 2 to 4.

The antibody according to the second aspect of the present invention may bind to any region of a peptide, which is not specifically limited as far as it binds to a peptide having amino acid residues described in any one of SEQ ID NOS: 2 to 4.

Preferably, it is an antibody that binds to a peptide having 16 amino acid residues described in SEQ ID NO: 2.

The characteristic feature of the antibody according to the second aspect of the present invention is to bind to the human low-molecular-weight CD14. This feature allows the antibody to be used in a kit according to the fourth aspect of the present invention or an assay according to the fifth aspect of the present invention.

Furthermore, the molecular weight of the human low-molecular-weight CD14 is different from that of the high-molecular-weight CD14, and also the amino acid sequence of the former is shorter than that of the latter. For this reason, the conformation of the low-molecular-weight CD14 in blood is different from that of the high-molecular-weight CD14, so that their reactivity with the antibody may be different from each other. Thus, it is conceivable that the antibody according to the second aspect of the present invention strongly binds to the low-molecular-weight CD14.

The phrase "binding to a peptide having amino acid residues described in any one of SEQ ID NOS: 2 to 4" means that the antibody specifically binds to a peptide as an antigen, the peptide having amino acid residues described in each of SEQ ID Numbers and shows a normal antigen-antibody reaction. For instance, the phrase "binding to a peptide having 16 amino acid residues described in SEQ ID NO: 2" means that the antibody specifically binds to a peptide as an antigen, the peptide having 16 amino acid residues described in SEQ ID NO: 2 and shows a normal antigen-antibody reaction. The representation of the antibody-antigen reaction can be identified by a agglutination method, sandwich method, solid-phase direct method or solid-phase binding method, competition method, and so on.

The dissociation constant (KD) of the antibody according to the second aspect of the present invention is, when the dissociation constant is expressed as affinity to the peptide or the low-molecular-weight CD14, preferably less than $10^{-7}$ M, more preferably $10^{-8}$ M or less, still more preferably $10^{-9}$ M or less.

In the preparation of the antibody according to the second aspect of the present invention, the peptide used as the antigen is a peptide that contains consecutive 8 or more amino acids of the amino acid residue described in any one of SEQ ID NOS: 2 to 4, preferably consecutive 10 or more, more preferably consecutive 12 or more, particularly preferably consecutive 16 or more amino acids. Furthermore, as far as the peptide contains consecutive 8 or more amino acids of the amino acid residue described in any one of SEQ ID NOS: 2 to 4, the other amino acid sequences are not limited. The entire amino acid sequence of the peptide is preferably derived from an amino acid sequence described in any one of SEQ ID NOS: 2 to 4.

The antibody according to the second aspect of the present invention is preferably an antibody prepared using a peptide as an antigen, the peptide having consecutive 8 or more amino acids of amino acid residues described in SEQ ID NO: 2. It is an antibody prepared using a peptide as an antigen, the peptide having preferably consecutive 10 or more, more preferably consecutive 12 or more, particularly preferably consecutive 16 or more amino acids.

The antibody according to the first aspect of the present invention and the antibody according to the second aspect of the second aspect of the present invention (hereinafter, they may be described as the antibodies of the present invention) may be polyclonal antibodies or monoclonal antibodies. The species of an animal from which the antibody of the present invention is originated are not specifically limited. In terms of facilitating the preparation of the antibody, a rabbit, goat, or the like is preferable. In addition, the immunoglobulin species may be used in any one of classes, subclasses, and isotypes.

Examples of a method of preparing a peptide to be used as an immunogen include a method using a generally-employed peptide synthesizer (Peptide Synthesizer 433A Type, Perkin-Elmer, Japan) or the like and a genetic recombination method ("New Cell Engineering Experiments Protocols," Ed. Department of Carcinostatic Research, The Institute of Medical Science, The University of Tokyo, Shujunsha).

For instance, a peptide having consecutive 8 or more amino acids of amino acid residues described in SEQ ID NO: 2 can be synthesized by an Fmoc method using a 433A Type peptide synthesizer. After deprotection with TFA and cutting out from the resin, the resultant is purified by using a C18 HPLC column (Capcell-pak, Shiseido Co., Ltd.), to thereby prepare the target peptide.

When the antigen is a protein, it can be directly used as an immunogen. However, when a peptide has 8 to 30 amino acid residues or less, the molecular weight of the peptide is small, it is not enough to use, as immunogen, in general. In this case, the peptide may be provided as an antigen by binding the peptide to a carrier or by using a Multiple Antigen Peptide (MAP) method. Then, an MAP peptide is prepared and provided with a molecular weight that allows the antigen to have immunogenicity.

Carriers to be bound to the peptides described above include carrier proteins and polymers. The carrier proteins used may be heteroproteins such as bovine serum albumin, keyhole limpet hemocyanin (KLH), thyroglobulin, and ovalbumin. Those carrier proteins utilize the functional groups of the side chain in an amino acid of a peptide or carrier protein or introduce a maleimide group, N-hydroxysuccinimide (NHS) group, or aldehyde group to allow the carrier to bind to the above peptide. Examples of the polymers include saccharides such as mannan and chitosan and polyvinylpyrrolidone (PVA). Those polymers may bind to the above peptides by means of adsorption or chemical binding as described above.

The antibody of the present invention can be prepared using the technologies known in the art (see, for example, Procedures of Immunological Experiments, The Japanese Society for Immunology, Ed., published by The Japanese Society for Immunology). For instance, a polyclonal antibody can be prepared by the following method.

Any one of the various animals can be immunized by a mixture of 20 to 1,000 μg of immunogen prepared as described above with an adjuvant such as a Freund's complete adjuvant, RIBI adjuvant, or ALUM. Examples of the various animals which can be used include a horse, sheep, goat, pig, rabbit, rat, and mouse. Immunization procedures which can be used include intramuscular administration, intradermal administration, subcutaneous administration, intraperitoneal administration, and lymph-node administration. A booster immunity can be given such that, every 1-4 weeks after first time administration, the immunogen mixed with the adjuvant such as a Freund's incomplete adjuvant, RIBI adjuvant, or ALUM is administrated similarly or the immunogen is intravenously administrated in a direct manner. An antiserum can be prepared from an immunized animal by a normal blood sampling method, for example, a method including: collecting blood from the carotid artery, auris vein, heart, leg vein, or the like; and separating the serum from the blood by means of centrifugation or the like. The resulting antiserum is subjected to a salting-out method involving the addition of ammonium sulfate, sodium sulfate, or the like to precipitate a γ-globulin fraction. Then, after the fraction has been dialyzed in an appropriate buffer, a purified polyclonal antibody of the fraction of IgG against a target peptide can be prepared using an affinity matrix of protein A, protein G, or the like capable of specifically purifying γ-globulin. In addition, specific purification can be performed by selecting an antibody that binds to the above antigen.

Furthermore, the monoclonal antibody can be prepared by the following method.

The antibody of the present invention can be prepared by: fusing immunocytes of an immunized animal with myeloma cells to prepare hybridomas; and selecting a clone that produces an antibody capable of binding to the above peptide from the hybridomas. Preferably, an immunogen is a peptide having consecutive 10 or more amino acid residues at positions 53 to 68. In addition, an immunogen is more preferably a peptide having consecutive 12 or more amino acids, particularly preferably a peptide having consecutive 16 amino acids.

Although a mammal to be immunized is not specifically limited, it is preferably selected in consideration of compatibility with myeloma cells to be used in cell fusion and preferably a mouse, rat, hamster, or the like. The myeloma cells which can be used are various kinds of cells well known in the art including myeloma cells P3, P3U1, SP2/O, NS-1, YB2/0, and Y3-Ag1, 2, and 3.

The immunization can be performed by a known method. For example, the immunization is performed by administering an antigen intraperitoneally, subcutaneously, intravenously, or into the foot pad. The antigen may be administered in combination with an adjuvant and it is preferable to administer the antigen in a plurality of times. The immunocytes are preferably spleen cells or cells derived from lymph node isolated several days, for example, 3 days after the final administration of the antigen. Immunocytes and myeloma cells can be fused using a known method such as the method of Milstein et al. (Methods in Enzymol., vol. 73, p. 3). For example, mention may be made of the method using polyethylene glycol (PEG) as a fusing agent, an electric field-induced cell fusion method, or the like. A mixing ratio of immunocytes and myeloma cells is not particularly limited as far as it allows the fusion. However, it is preferable to make the amount of myeloma cells 1/10 to the equivalent relative to immunocytes. In the method in which cell fusion is performed using PEG (mean molecular weight: 1,000 to 4,000), the concentration of PEG is not particularly limited. However, it is preferable that fusion be performed at a concentration of 50%. An auxiliary such as dimethyl sulfoxide (DMSO) may be added as an enhancer of the fusion efficiency. The fusion is started by the addition of a PEG solution warmed at 37° C. to mixed cells and is terminated by the addition of a culture medium after reacting the solution and the cells for 1 to 5 minutes. The hybridomas created by the fusion are incubated for 1 to 7 days in a selection medium such as a culture medium containing hypoxanthine, thymidine, and aminopterin (HAT medium) to separate them from nonfused cells.

The obtained hybridomas are further selected by antibodies produced by them. A selected hybridoma is converted into a monoclonal by a known limiting dilution method to establish a monoclonal antibody producing hybridoma. Any one of the known methods may be used as the method of detecting the activity of an antibody that the hybridoma produces. Examples of the methods include an ELISA, agglutination reaction, and radio immunoassay. Examples of the established hybridoma may be cultivated by a known method and a monoclonal antibody may be obtained from the culture supernatant. In addition, the hybridoma is administered to a mammal having compatibility therewith to allow proliferation, and the proliferated hybridoma is obtained from the ascites. Purification of the antibody can be performed using a known purification method such as salting out, gel filtration, ion exchange chromatography, or affinity chromatography.

Furthermore, as described in the aspect below, the antibody of the present invention can be used in the assay kit for human low-molecular-weight CD14 of the present invention, it is conceivable that an antibody that binds to the human low-molecular-weight CD14 but not to human high-molecular-weight CD14 may be prepared.

It is conceivable that the antibody that binds to the human low-molecular-weight CD14 but not to human high-molecular-weight CD14 may be obtained by preparing an antibody using the low-molecular-weight CD14 as an antigen and selecting an antibody that does not bind to the high-molecular-weight CD14.

A method of preparing the low-molecular-weight CD14 is described in Example 16 of WO 01/72993. In addition, using the antibody of the present invention, the low-molecular-weight CD14 can be prepared by specific purification from human serum, preferably from the serum of a patient suffering from sepsis.

For selecting the antibody that does not bind to the high-molecular-weight CD14, the binding between the resulting antibody and the high-molecular-weight CD14 may be assayed by a agglutination method, sandwich method, solid-phase direct method or solid-phase binding method, competition method, or the like. Those methods will be described later.

The high-molecular-weight CD14 may be prepared using an antibody specific to the high-molecular-weight CD14, which is described in Example 5 of WO 01/22085.

It is also conceivable that the antibody may be prepared by preparing and selecting an antibody that does not bind to the high-molecular-weight CD14 by the same way as described above using a peptide as an antigen, the peptide having a part of the amino acid sequence of human CD14. The "peptide having a part of the amino acid sequence of human CD14" means, for example, each peptide that contains consecutive 8 or more amino acids in the sequence of 16 amino acids described in SEQ ID NO: 2.

According to a third aspect of the present invention, there is provided a assay kit for human low-molecular-weight CD14, which contains an antibody that binds to at least one of human low-molecular-weight CD14 or a fragment of the antibody and which directly assays the human low-molecular-weight CD14 in a specimen without detecting human high-molecular-weight CD14.

The kit of the present invention contains an antibody that binds to at least one of human low-molecular-weight CD14 or a fragment of the antibody and directly assays the human low-molecular-weight CD14 in a specimen. In addition, the kit detects the human low-molecular-weight CD14 as an analyte but does not detect human high-molecular-weight CD14, so that the human low-molecular-weight CD14 can be directly assayed. The "fragment of the antibody" means Fab, Fab', or F(ab')$_2$ of the antibody.

The assay kit for human low-molecular-weight CD14 of the present invention is not specifically limited as far as it contains an antibody that binds to at least one of human low-molecular-weight CD14 or a fragment of the antibody and directly assays the human low-molecular-weight CD14 in a specimen. Preferably, it is an assay kit for human low-molecular-weight CD14 containing the antibody of the present invention or a fragment of the antibody as the antibody that binds to the human low-molecular-weight CD14 or the fragment of the antibody. More preferably, it is an assay kit for human low-molecular-weight CD14 including an antibody prepared using a peptide as an antigen, the peptide having amino acid residues described in any one of SEQ ID NOS: 2 to 4, or a fragment of the antibody. In addition, preferably, it is an assay kit for human low-molecular-weight CD14 including an antibody that binds to a peptide having amino acid residues described in any one of SEQ ID NOS: 2 to 4 or a fragment of the antibody as an antibody that binds to the human low-molecular-weight CD14 or a fragment of the antibody. Particularly preferably, it is an assay kit for human low-molecular-weight CD14 including an antibody prepared using a peptide as an antigen, the peptide having amino acid residues described in SEQ ID NO: 2 or a fragment of the antibody, or an antibody that binds to a peptide having 16 amino acid residues described in SEQ ID NO: 2 or a fragment of the antibody, as an antibody that binds to human low-molecular-weight molecule or a fragment of the antibody.

Furthermore, the principle of the assay is not specifically limited as far as the assay is a method of immunologically assaying human low-molecular-weight CD14 using the antibody or the fragment thereof.

As an example of the principle of the assay, an assay kit for human low-molecular-weight CD14 (hereinafter, it may be described as a sandwich immunoassay kit), which determines the human low-molecular-weight CD14 by a sandwich immunoassay using the "antibody that binds to a peptide having 16 amino acid residues described in SEQ ID NO: 2" as a preferred example of the antibody according to the second aspect of the present invention, will be described concretely.

A well-known method may be used as the sandwich immunoassay. The principle, application, and modification of the assay are described in, for example, "Hypersensitive Enzyme Immunoassay", Eiji Ishikawa Ed., Center for Academic Publications Japan (1993), "New Utilization Examples and Applications to Diagnostic Reagent/Drug Development of Immunoassay", Immunoassay Development Research Society, Keiei-Kyoiku Shuppan, and "Enzyme Immunoassay (3rd Ed), Eiji Ishikawa Ed., Igaku-Shoin Ltd. (1987).

Furthermore, the sandwich immunoassay kit of the present invention contains an antibody that binds to a peptide having 16 amino acid residues described in SEQ ID NO: 2. The characteristic features of the antibody that binds to the peptide having 16 amino acids described in SEQ ID NO: 2, a method of preparing such an antibody, and so on are just as the same as those according to the first aspect of the present invention. The antibody may be, but not specifically limited, a polyclonal antibody or a monoclonal antibody.

The sandwich immunoassay is a method using two or more kinds of antibodies that recognize different sites on a protein to be usually assayed, where the assay is performed by forming an antibody-antigen-antibody complex.

First, an insoluble carrier coupled with a first antibody is prepared and is then provided as a solid phase or a reaction place. A specimen is added to the insoluble carrier provided as the solid phase and then they are allowed to react with each other. After they have been reacted for a predetermined time period, the solid phase is washed to remove an unbound substance therefrom. Subsequently, a labeled second antibody is added. After the mixture has been reacted for a predetermined time period, the labeled antibody that did not form a complex is removed by washing and then the amount of the complex bound to the solid phase is qualitatively or quantitatively determined on the basis of the labeled product in a specific manner. The sandwich method may use any one of a method including two steps as described above (double-step method) and a method including the step of simultaneously adding both an antigen and a labeled antibody (single-step method).

In the sandwich immunoassay kit of the present invention, the assay is performed by forming a complex of the "antibody that binds to a peptide having 16 amino acid residues described in SEQ ID NO: 2"—human low-molecular-weight CD14—the "second binding substance that binds to the human low-molecular-weight CD14".

The format of the sandwich immunoassay kit of the present invention includes: an insoluble carrier bound with an antibody that binds to a peptide having 16 amino acid residues described in SEQ ID: 2 and a second binding substance that binds to a labeled low-molecular-weight CD14 (hereinafter, it may be simply described as a second binding substance); or an insoluble carrier bound with a second binding substance and an antibody that binds to a labeled peptide having 16 amino acid residues described in SEQ ID NO: 2.

Examples of the second binding substance include an antibody that binds to the low-molecular-weight CD14. The antibody that binds to the low-molecular-weight CD14 may be a polyclonal antibody or a monoclonal antibody and is not specifically limited. The monoclonal antibody is preferable with respect to affinity to the sandwich immunoassay using the antibody that binds to the peptide having 16 amino acid residues described in SEQ ID NO: 2. Furthermore, the second binding substance may be a fragment of the monoclonal antibody. The fragment of the antibody is Fab, Fab', or F(ab')$_2$ of the monoclonal antibody.

The antibody that binds to the low-molecular-weight CD14 (hereinafter, it may be described as a second antibody) may be an antibody that specifically binds to the low-molecular-weight CD14 or an antibody that binds to high-molecular-weight CD14 and is not specifically limited. Preferably, it is an antibody that binds to a site different from that of the antibody of the present invention. The second antibody is an antibody that binds to a region except a region corresponding to 16 amino acids described in SEQ ID NO: 2 of the low-molecular-weight CD14 when an antibody that binds to a peptide having 16 amino acid residues described in SEQ ID NO: 2 is used as the antibody of the present invention. More preferably, the second binding substance described above is: an antibody that binds to any one region of amino acid residues at positions 1 to 52 of the human high-molecular-weight CD14 or a fragment of the antibody; or an antibody competing with or showing cross-reactivity with an antibody that binds to any one region of amino acid residues at positions 1 to 52 of the human high-molecular-weight CD14 or a fragment of the antibody. Particularly preferably, the second binding substance described above is: an antibody that binds to any one amino acid residue at positions 17 to 26 of the human low-molecular-weight CD14 or a fragment of the antibody; or an antibody competing with (showing cross-reactivity with) an antibody that binds to any one amino acid residue at positions 17 to 26 of the human low-molecular-weight CD14 or a fragment of the antibody.

A polyclonal antibody or monoclonal antibody may be prepared, for example, using high-molecular-weight CD14, low-molecular-weight CD14, a mixture of high-molecular-weight CD14 with low-molecular-weight CD14, or recombinant CD14 as an antigen, as in the case with the method according to the first aspect of the present invention. An exemplified method of preparing a second antibody using a mixture of high-molecular-weight CD14 with low-molecular-weight CD14, and recombinant CD14 as antigens will be shown in Example 3 described below.

In addition, it is preferable to select a second antibody such that, before actually conducting the assay, just as in the case with Example 3 described later, a system for the sandwich method including an antibody that binds to a peptide having 16 amino acid residues described in SEQ ID NO: 2 and an antibody which is a candidate for the second antibody is preliminary constructed to confirm the sensitivity of the assay.

Furthermore, the fragments of the antibody: Fab, Fab', and F(ab')$_2$ can be prepared by a well-known method ("Hypersensitive Enzyme Immunoassay", written by Eiji Ishikawa, p. 25-40, Center for Academic Publications Japan (1993)).

In the sandwich immunoassay, the assay may be performed by a competition method as an alternate of the above method. It is a method of allowing an antigen in a specimen to compete with a labeled antigen or a labeled antigen analogue during the formation of an antibody-antigen-antibody complex.

In the sandwich immunoassay kit of the present invention, the assay is performed by forming a complex of the "antibody that binds to a peptide having 16 amino acid residues described in SEQ ID NO: 2"—labeled human low-molecular-weight CD14 (or an analogue thereof)—the "second binding substance that binds to human low-molecular-weight CD14".

The format of the competition method for the sandwich immunoassay kit of the present invention includes: an insoluble carrier bounded with an antibody that binds to a peptide having 16 amino acid residues described in SEQ ID NO: 2; a second binding substance; and labeled human low-molecular-weight CD14 or labeled human low-molecular-weight CD14 analogue, or includes: an antibody that binds to a peptide having 16 amino acid residues described in SEQ ID NO: 2; an insoluble carrier bound with a second binding substance; and labeled human low-molecular-weight CD14 or labeled human low-molecular-weight CD14 analogue.

Examples of the human low-molecular-weight CD14 analogue include a soluble polypeptide having amino acids at positions 1 to 285 on the N-terminal of the human CD14 (hereinafter, described as sCD14(1-285)) and a recombinant polypeptide having amino acids at positions 1 to 307 on the N-terminal of the human CD14 where serine at position 286 is substituted with cysteine (hereinafter, described as sCD14 (1-307)S286C). In the assay system, however, the human low-molecular-weight CD14 analogue is not specifically limited as far as it is a substance capable of competing with the human low-molecular-weight CD14 in a specimen. The methods of preparing sCD14(1-285) and sCD14(1-307) S286C are described in WO 01/72993.

Furthermore, in the sandwich immunoassay, the assay may be performed by taking advantage of the second specific binding as an alternative method. It is a method of conducting an assay by forming a complex of antibody-antigen-antibody-second specific binding substance-specific binding partner of the second specific binding substance (hereinafter, it may be described as a second specific binding partner).

In the sandwich immunoassay kit of the present invention, the assay is performed by forming a complex of the "antibody that binds to a peptide having 16 amino acid residues described in SEQ ID NO: 2"—human low-molecular-weight CD14-the "second binding substance that binds to human low-molecular-weight CD14"—second specific binding substance—second specific binding partner, or by forming a complex of the "second binding substance that binds to human low-molecular-weight CD14"—human low-molecular-weight CD14—the "antibody that binds to a peptide having 16 amino acid residues described in SEQ ID NO: 2"—second specific binding substance—second specific binding partner.

The format taking advantage of the second specific binding of the sandwich immunoassay kit of the present invention includes: an antibody labeled with a second specific binding substance that binds to a peptide having 16 amino acid residues described in SEQ ID NO: 2; a second specific binding substance that binds to labeled low-molecular-weight CD14; and an insoluble carrier bound with a second specific binding partner, or includes: a labeled antibody that binds to a peptide having 16 amino acid residues described in SEQ ID NO: 2; a second binding substance that binds to low-molecular-weight CD14 labeled with a second specific binding substance; and an insoluble carrier bound with a second specific binding partner.

Examples of the combination of the second specific biding substance and the second specific binding partner include: an antigen and an antibody thereof; a ligand and a receptor thereof; substance containing some sugars and lectin; and biotin and avidin or streptavidin.

Furthermore, examples of the sandwich immunoassay include: an assay with the formation of a complex of antibody-antigen-antibody-anti-immunoglobulin antibody by taking advantage of an antibody against an antibody, i.e., an anti-immunoglobulin antibody; and an assay with the formation of anti-immunoglobulin antibody-antibody-antigen-antibody-second specific binding substance-second specific binding partner by taking advantage of anti-immunoglobulin antibody and second specific binding.

The sandwich immunoassay kit of the present invention conducts an assay by: forming a complex of the "antibody that binds to a peptide having 16 amino acid residues described in SEQ ID NO: 2"—human low-molecular-weight CD14-the "second binding substance that binds to human low-molecular-weight CD14"—anti-immunoglobulin antibody; forming a complex of the "antibody that binds to a peptide having 16 amino acid residues described in SEQ ID NO: 2"—human low-molecular-weight CD14—the "second binding substance that binds to human low-molecular-weight CD14"—anti-immunoglobulin antibody; forming anti-immunoglobulin antibody-the "antibody that binds to a peptide having 16 amino acid residues described in SEQ ID NO: 2"—human low-molecular-weight CD14—the "second binding substance that binds to human low-molecular-weight CD14"—second specific binding substance-second specific binding partner; forming anti-immunoglobulin antibody—the "second binding substance that binds to human low-molecular-weight CD14"—human low-molecular-weight CD14—the "antibody that binds to a peptide having 16 amino acid residues described in SEQ ID NO: 2"-second specific binding substance-second specific binding partner, or the like.

Any sandwich immunoassay is within the scope of the assay of the present invention even though a solid phase, a labeled substance, or the like is formed by taking advantage of the second specific binding as far as it performs an assay by forming a complex of the "antibody that binds to a peptide having 16 amino acid residues described in SEQ ID NO: 2"—human low-molecular-weight CD14—the "second binding substance that binds to human low-molecular-weight CD14".

In other words, any sandwich immunoassay kit of the present invention is within the scope of the kit of the present invention as far as it includes an antibody that binds to a peptide having 16 amino acid residues described in SEQ ID NO: 2.

An insoluble carrier used in the sandwich immunoassay kit of the present invention may be beads, latex particles, magnetic particles, a plate, a tube, a membrane, or the like. Materials of the beads, plate, or tube include polystyrene, nylon, glass, silicone rubber, stainless steel, and plastic. The membrane may be cellulose, a cellulose derivative, nitrocellulose, a porous synthetic polymer, a glass fiber, cloth, a nonwoven fabric, filter paper, or the like. The beads, latex particles, magnetic particles, or the like may be used in a spherical shape. A spherical shape is advantageous in saving a space in storage. The plate or tube may be used in the form of a well. A well form is advantageous in that it will be accepted to a commercial automatic measuring instrument, plate reader, or the like. The membrane can be used for an immunochromatographic method or a flow through method described later.

The antibody that binds to a peptide having 16 amino acid residues described in SEQ ID NO: 2, the second binding substance, the second specific binding substance or the partner thereof, or the anti-immunoglobulin antibody can be bound to the insoluble carrier by a thermal adsorption method, chemical binding method, or the like.

In addition, it is preferable to subject the non-adsorption surface of the insoluble carrier being free of the above substance to a blocking treatment with any substance that does not affect the assay system because the treatment will impart increased specificity or sensitivity to the assay system. The substances that do not affect the assay system include: proteins such as BSA and casein; and surfactants such as Tween 20 and NP-40.

Labels to be used in the sandwich immunoassay kit of the present invention include: enzymes such as peroxidase, alkali phosphatase, $\beta$-$_D$-galactosidase, oxidase, and urokinase; chemiluminescent substances such as acridinium or a derivative thereof and aequorin or a modified product thereof; fluorescent substances such as FITC; dyestaff; gold colloid; colored latex; and isotopes.

For instance, in the case of using peroxidase as an enzyme, 3,3',5,5'-tetrabenzidine or 1,2-phenylene diamine may be exemplified as a chromogenic substrate. In the case of using alkali phosphatase, 4-nitrophenylphosphate may be exemplified as a chromogenic substrate. In the case of using $\beta$-$_D$-galactosidase, 2-nitrophenyl$\beta$-$_D$-glactoside may be exemplified as a chromogenic substrate.

Enzyme-labeling to the antibody that binds to a peptide having 16 amino acid residues described in SEQ ID NO: 2, the second binding substance, the second specific binding substance or the partner thereof, or the anti-immunoglobulin antibody can be performed by a two-step glutaraldehyde method, periodic acid method, maleimide method, pyridyl disulfide method, or the like.

Apart from the enzyme, a well-known technology such as a thermal adsorption method or chemical binding method may be available in the labeling.

Enzyme-labeling is preferable because it can be assayed using conventional chrometry system if any chromogenic substrate exemplified above is used and because the sensitivity thereof is comparatively high. Furthermore, the labeling used in a simple kit such as a kit utilizing an immunochromatographic method or flow through method described later is preferable because dye stuff, gold colloid, or colored latex can be visually observed.

The sandwich immunoassay kit of the present invention is characterized in that an assay is performed by a sandwich immunoassay and includes an antibody that binds to a peptide having 16 amino acid residues described in SEQ ID NO: 2. The sandwich immunoassay can use the well-known technology as described above. In addition to the above concrete description, any kit based on the sandwich immunoassay is within the scope of the sandwich immunoassay kit of the present invention and is not specifically limited as far as the kit includes an antibody that binds to a peptide having 16 amino acid residues described in SEQ ID NO: 2. In other words, it is enough for the kit to contain an antibody that binds to a peptide having 16 amino acid residues described in SEQ ID NO: 2 and a reagent required for the sandwich immunoassay. In addition, no content is restricted as far as it does not inhibit the assay results based on the principle of the assay.

For instance, a buffer or diluent of a specimen, labeled antibody, or the like, a chromogenic substrate (see the above description) suitable for an enzyme when the enzyme is used for a labeled antibody, a blocking agent, a stopping reagent, or a washing solution may be exemplified as an optional constitutional element. In addition, a standard substance may be also exemplified as an optional constitutional element. The standard substances include human low-molecular-weight CD14 and human low-molecular-weight CD14 analogues.

Furthermore, a kit that utilizes an immunochromatographic method or a flow through method on the basis of a sandwich immunoassay as a principle of the assay is also within the scope of the sandwich immunoassay kit of the present invention.

The immunochromatographic method is a method where an antigen provided as a test substance in a specimen moves along a test strip to an insoluble carrier on which an antibody is immobilized while the antigen reacts with a labeled antibody being arranged in the test strip so as to be able to move, and then a complex of the antibody-antigen-antibody is formed on the insoluble carrier. In general, the antigen can be assayed by a single step of dropping the specimen on the test strip.

For instance, apparatuses for the immunochromatographic method are disclosed in JP 01-063865 A, WO 88/08534, and WO 90/09592. In addition, apparatuses for the immunochromatographic method having flow channels with different developing speeds are disclosed in WO 89/03993 and WO 99/27364, and for example, the apparatuses can be applied such that a labeled antibody can be reacted after the formation of a complex by allowing the reaction between the immobilized antibody and the antigen.

An example that utilizes the immunochromatographic method of the sandwich immunoassay kit of the present invention will be described below.

For instance, a device (i.e., a kit) is a test strip on which a sample-adding part, a reagent part, a detection part, and an absorbing part are provided such that a liquid specimen added on the sample-adding part is allowed to move along those parts in that order. It is sufficient that a labeled second binding substance be impregnated in the reagent part and an insoluble carrier bound with an antibody that binds to a peptide having 16 amino acid residues described in SEQ ID NO: 2 be arranged on the detection part.

The specimen added on the sample-adding part absorbs the labeled second binding substance at the reagent part. The human low-molecular-weight CD14 reacts with the labeled second binding substance to form a complex while they move to the detection part. On the detection part, the complex reacts with the antigen that binds to the peptide having 16 amino acid residues described in SEQ ID NO: 2, resulting in the formation of a complex of the "antibody that binds to the peptide having 16 amino acid residues described in SEQ ID NO: 2"—human low-molecular weight CD14—the "second binding substance that binds to human low-molecular-weight CD14" on an insoluble carrier. Any substance and reagent in the specimen, which are not involved in the reaction, move to the absorbing part. The label of the complex formed on the detection part may be determined, particularly may be visually determined.

A porous carrier or the like may be used as a test strip. The porous carrier may be, for example, nitrocellulose, cellulose, a cellulose derivative, nylon, a nylon fiber, a glass fiber, or a porous synthetic polymer.

Part of the test strip may be directly used as the sample-adding part or reagent part. Alternatively, for example, cellulose filter paper, a glass fiber, cloth, non-woven fabric, porous synthetic polymer, or the like may be used depending on the amount of the sample or the dose of the reagent.

Cellulose, a cellulose derivative, nitrocellulose, a porous synthetic polymer, a glass fiber, cloth, non-woven fabric, filter paper, or the like may be used for the detection part as described above.

A water-absorbable material may be used for the absorbing part. Examples of the water-absorbable material include: an absorbent polymer such as sponge; cellulose filter paper; and filter paper.

The above is one of the examples of the immunochromatographic method. A reference part for confirming the progress of a reaction may be added, or the test strip may be provided with a support or covered with an external cover. However, the kit of the present invention is not limited to them.

Furthermore, as described in the explanation about the sandwich immunoassay, a kit for an immunochromatographic method, by which a complex of the "antibody that binds to a peptide having 16 amino acid residues described in SEQ ID NO: 2"—human low-molecular-weight CD14—the "second binding substance that binds to human low-molecular-weight CD14" is formed on an insoluble carrier and an assay is performed by forming a complex that utilizes an anti-immunoglobulin antibody and second specific binding, is also within the scope of the sandwich immunoassay kit of the present invention.

The flow through method is a method by which an antigen provided as a test substance forms an antibody-antigen-antibody complex together with a solution in a specimen on a membrane provided as an insoluble carrier. At this time, a substance failed to be fixed on the membrane is generally removed by perpendicularly passing through the membrane from the front to the back.

WO 88/01603 discloses an apparatus based on a multi-step method by which a specimen, a regent, and a cleaner are dropped onto a membrane.

JP 06-273419 A discloses a method being improved as a single-step method in which a multi-layered membrane is formed and a regent part is provided thereon so as to conduct the assay only by dropping a specimen.

Hereinafter, an example of the sandwich immunoassay kit of the present invention using a flow through method will be described.

For instance, a device (i.e., a kit) is a kit on which a sample-adding part, a reagent part, a detection part, and an absorbing part are layered one on top of another such that a liquid specimen added on the sample-adding part is allowed to move along those parts in that order. It is sufficient that a labeled second binding substance be impregnated in the reagent part and an insoluble carrier bound with an antibody that binds to a peptide having 16 amino acid residues described in SEQ ID NO: 2 be arranged on the detection part.

The specimen added on the sample-adding part passes through the sample-adding part perpendicularly from the top to back of the membrane (hereinafter, the same holds true for the sample movement) and then absorbs the second binding substance at the reagent part. The human low-molecular-weight CD14 reacts with the labeled second binding substance to form a complex while they move to the detection part. On the detection part, the complex reacts with the antigen that binds to the peptide having 16 amino acid residues described in SEQ ID NO: 2, resulting in the formation of a complex of the "antibody that binds to the peptide having 16 amino acid residues described in SEQ ID NO: 2"—human low-molecular weight CD14—the "second binding substance that binds to human low-molecular-weight CD14" on an insoluble carrier. Any substance and reagent in the specimen, which are not involved in the reaction, move to the absorbing part. The label of the complex formed on the detection part may be determined, particularly may be visually determined. The label can be visually observed in a simple manner if a device is designed such that the detection part is detachable from the sample-adding part and reagent part or from the absorbing part. In addition, the label can be visually observed from the sample-adding part if each of the sample-adding part and reagent part is made of a translucent material, or from the lower side if the absorbing part is arranged above the detection part (the sample-adding part side) as in the case of JP 06-0273419 A.

The same members as those of the immunochromatographic method can be applied and each member may be formed like a membrane to allow the solution in a specimen to move.

The above is one of the examples of the flow through method. A reference part for confirming the progress of a reaction may be added, or each member may be provided with a support or covered with an external cover. However, the sandwich immunoassay kit of the present invention is not limited to them.

Furthermore, as described in the explanation about the sandwich immunoassay, in addition to the formation of a complex of the "antibody that binds to a peptide having 16 amino acid residues described in SEQ ID NO: 2"—human low-molecular-weight CD14—the "second binding substance that binds to human low-molecular-weight CD14" on an insoluble carrier, a kit for the flow through method that conducts the assay by forming a complex that utilizes the anti-immunoglobulin antibody and the second specific binding is also within the scope of the sandwich immunoassay kit of the present invention.

Furthermore, the sandwich immunoassay kit of the present invention can be available to an assay based on a MEDIA method (JP 05-264552 A) of electrochemically measuring signals from a label and an assay based on an immunoassay method ("Bioscience and Industry", vol. 61, p. 449-454, 2003) using a microchip. The assay kits using those principles are within the scope of the sandwich immunoassay kit of the present invention as far as they are characterized by their assays based on the sandwich immunoassay and include an antibody that binds to a peptide having 16 amino acid residues described in SEQ ID NO: 2.

The sandwich immunoassay kit of the present invention is characterized by including an antibody that binds to a peptide having 16 amino acid residues described in SEQ ID NO: 2 and is capable of specifically determining low-molecular-weight CD14. A specimen to be used in the sandwich immunoassay kit of the present invention is preferably an aqueous specimen. Particularly preferable examples of the specimen include blood, blood component such as serum or plasma, urine or other body fluids, cell culture supernatant, and column eluent. They are useful for the determination on low-molecular-weight CD14 in them. However, from the specimens except the human blood component, such as human urine or other body fluids, blood components, urine, or other body fluids form species except a human being, cell culture supernatant, and column eluent, proteins, polypeptides, or the like which are analogous to the low-molecular-weight CD14 may be also assayed as well as the low-molecular-weight CD14. Any assay kit for the above polypeptides, or the like which are analogous to the low-molecular-weight CD14 is also within the scope of the sandwich immunoassay kit of the present invention as far as they each include an antibody that binds to a peptide having 16 amino acid residues described in SEQ ID NO: 2.

Furthermore, in the above explanation, the fragment Fab, Fab', or (Fab')$_2$ of the "antibody that binds to a peptide having 16 amino acid residues described in SEQ ID NO: 2" may be used instead of the "antibody that binds to a peptide having 16 amino acid residues described in SEQ ID NO: 2".

In the above description, the concrete examples using the "antibody that binds to a peptide having 16 amino acid residues described in SEQ ID NO: 2" have been described as preferred examples of the antibody according to the second aspect of the present invention. However, the antibody according to the first aspect of the present invention, the antibody according to the second aspect of the present invention except the "antibody that binds to a peptide having 16 amino acid residues described in SEQ ID NO: 2", or the fragment Fab, Fab', or (Fab')$_2$ of those antibodies may be also used.

Preferable is a sandwich immunoassay kit using the antibody of the second aspect of the present invention. More preferable is a sandwich immunoassay kit using the "antibody that binds to a peptide having 16 amino acid residues described in SEQ ID NO: 2".

Furthermore, principles for the assay include an agglutination method, solid-phase binding method, and solution reaction method in addition to the sandwich immunoassay method. Depending on those methods, the respective kits may be constructed such that each of them contains the antibody that binds to at least one of human low-molecular-weight CD14 or the fragment of the antibody, preferably the antibody of the present invention or the fragment of the antibody.

In the agglutination method, the antibody is bound on the surface of particles and the presence of the antigen cause the particles to agglutinate, so that the antigen can be qualitatively or quantitatively determined in a specific manner in reference to the degree of agglutination of the particles.

An agglutination immunoassay kit of the present invention conducts the assay by forming the "antibody of the present invention"—human low-molecular-weight CD14 and causing the agglutination thereof.

The format of the agglutination immunoassay kit of the present invention includes particles to the surface of which the antibody of the present invention binds.

The particles used may be those generally used, including latex, red blood cells (e.g., sheep red blood cells), gelatin, micro beads, carbon particles, or the like.

The solid-phase binding method is a method of conducting the assay by the formation of a complex between an antibody and an antigen on a solid phase. An antigen-containing specimen is adsorbed in an insoluble carrier (i.e., solid phase, the same shall apply hereinafter). Next, a labeled antibody is added and the mixture is reacted to qualitatively or quantitatively determine the amount of the complex bound on the solid phase in a specific manner on the basis of the labeled product.

Furthermore, as a competition method, an antigen analogue is adsorbed on an insoluble carrier to allow the labeled antigen to compete with the reaction with the antigen in the specimen to determine the amount of the labeled antibody bound to the antigen analogue. Furthermore, as an alternative method of the competition method, the antibody is adsorbed in the insoluble carrier and the reaction with the antigen in the specimen is competed with the labeled antigen analogue to determine the amount of the labeled antigen analogue bound to the antibody.

In the solid-phase binding immunoassay kit of the present invention, an assay is performed by forming an "antibody of the present invention"—human low-molecular-weight CD14 complex, an "antibody of the present invention"—labeled human low-molecular-weight CD14 (or an analogue thereof) complex, or a "labeled antibody of the present invention"—human low-molecular-weight CD14 (or an analogue thereof) complex.

The format example of the solid-phase binding immunoassay kit of the present invention: includes the antibody of the present invention, an insoluble carrier, and a reagent for adsorbing a specimen on the insoluble carrier; or includes the antibody of the present invention and an insoluble carrier bound with labeled human low-molecular-weight CD14 (or an analogue thereof); or includes an insoluble carrier bound with the labeled antibody of the present invention and an insoluble carrier bound with labeled human low-molecular-weight CD14 (or an analogue thereof).

The insoluble carrier, human low-molecular-weight CD14 analogue, and labeling and adsorbing regents are the same as those described in the explanation of the sandwich immunoassay kit.

A solution-reaction method may be a method of qualitatively or quantitatively determining low-molecular-weight CD14 in a specific manner by: making a reaction between an antigen and a labeled antibody in a liquid phase; and then separating an antigen-antibody complex from the antigen and antibody by a coagulation process with the antibody or by physical and chemical procedures.

The format example of the solution-reaction immunoassay kit performs an assay such that a complex of the "labeled antibody of the present invention"—human low-molecular-weight CD14 is formed in a liquid phase and then an unbound labeled antibody is removed therefrom.

The format example of the solution-reaction immunoassay kit of the present invention includes the labeled antibody of the present invention.

In addition, in the above explanation, the "fragment of the antibody of the present invention, Fab, Fab', or (Fab')$_2$" may be used instead of the "antibody" of the present invention.

The examples of the assay kit of the present invention have been described above on the basis of their assay principles. However, the kit of the present invention is not limited to those principles. As far as an assay kit contains an antibody that binds to at least one human low-molecular-weight CD14 or a fragment of the antigen, the assay kit is within the scope of the assay kit of the present invention. For the principles of the immunoassay, the technologies well known in the art are available. "Hypersensitive Enzyme Immunoassay", Eiji Ishikawa Ed., Center for Academic Publications Japan (1993), "New Utilization Examples and Applications to Diagnostic Reagent/Drug Development of Immunoassay", Immunoassay Development Research Society, Keiei-Kyoiku Shuppan, and "Enzyme Immunoassay (3rd Ed), Eiji Ishikawa Ed., Igaku-Shoin Ltd. (1987), which are mentioned above, may be also referred.

The level of low-molecular-weight CD14 which can be specifically determined by the kit of the present invention increases in a patient suffering from sepsis. Thus, the assay of low-molecular-weight CD14 will be provided as a diagnostic index of sepsis and the kit of the present invention is useful for diagnosis of sepsis.

According to a fourth aspect of the present invention, there is provided an assay method for low-molecular weight CD14 with which the assay of human low-molecular-weight CD14 in a specimen is directly conducted using an antibody that binds to at least one of human low-molecular-weight CD14 for detecting the human low-molecular-weight CD14 without detecting human high-molecular-weight CD14.

The assay method of the present invention is a method for the assay of human low-molecular-weight CD14 for detecting the human low-molecular-weight CD14 without detecting human high-molecular-weight CD14 and uses an antibody that binds to at least of one of the human low-molecular-weight CD14 to directly determine the human low-molecular-weight CD14 in a specimen. Preferably, it is a method for the assay of low-molecular-weight CD14 using the antibody of the present invention. More preferably, it is a method for the assay of low-molecular-weight CD14 using an antibody prepared using a peptide as an antigen, the peptide having amino acid residues described in any one of SEQ ID NOS: 2 to 4. In addition, it is preferably a method for the assay of low-molecular-weight CD14 using an antibody that binds to a peptide having amino acid residues described in any one of SEQ ID NOS: 2 to 4. It is particularly preferably a method for the assay of low-molecular-weight CD14 using an antibody prepared using a peptide as an antigen, the peptide having amino acid residues described in SEQ ID NO: 2, or using an antibody that binds to a peptide having 16 amino acid sequences described in SEQ ID NO: 2. In the above explanation, furthermore, the "fragment of the antibody, Fab, Fab', or (Fab')$_2$" may be used instead of the "antibody".

Preferably, furthermore, it is a method for a low-molecular-weight CD14 assay with which human low-molecular-weight CD14 is determined by a sandwich immunoassay.

The antibody of the present invention may be used as an immobilized antibody, labeled antibody, or the like. In addition, a method for the assay that utilizes second specific binding and an anti-immunoglobulin antibody is also included. In this case, the antibody of the first aspect of the present invention can be used as a free antibody, an antibody binding to a second specific binding substance or to a second specific binding partner, or the like.

The method for the assay of the present invention may be a non-competitive or competitive method of sandwich immunoassay, and also the measurement with an immunochromatographic method or a flow-through method may be included.

Furthermore, the principle of the assay method of the present invention is not limited to the sandwich immunoassay and other examples thereof include an agglutination method, a solid-phase binding method, and a solution reaction method.

The details are as described in the third aspect of the present invention.

According to a fifth aspect of the present invention, there is provided a diagnostic method for sepsis by which human low-molecular-weight CD14 is directly assayed.

The diagnostic method for sepsis directly assays the low molecular weight CD14.

The method of directly assaying the low-molecular-weight CD14 is as described in the fourth aspect of the present invention. Furthermore, the diagnosis can be performed using the kit described in the third aspect of the present invention.

As described in Examples 3, 10, and 11 below, the assay of the low-molecular-weight CD14 in blood from each of normal individuals and various kinds of patients confirmed that a patient suffering from sepsis specifically showed a high level of low-molecular-weight CD14. This fact means that the result obtained by the assay using the above kit can be used as an index in the diagnosis of sepsis. For instance, the level of low-molecular-weight CD14 in blood of a patient is determined and is then compared with the standard level of normal individuals obtained, for example, by averaging up their measurements, or with the range of the levels of the normal individual. For instance, the average+2SD or 3SD of normal individuals is used as a cut-off level and, when the level of low-molecular-weight CD14 is higher than such a level, it is defined as a positive index. In addition, an index for the diagnosis can be also provided by comparing the measured level of low-molecular-weight CD14 of each individual with the levels of low-molecular-weight CD14 of normal individuals and patients suffering from sepsis or the standard levels obtained by standardizing those levels in advance. For instance, the low-molecular-weight CD14 level of a normal individual is defined as of 0 to 0.1 µg/ml and the level of a patient suffering from sepsis is defined as of 0.2 µg/mL or more, followed by comparing with the measured level to provide a negative, pseudo positive, or positive index.

According to a sixth aspect of the present invention, there is provided a peptide having amino acid residues described in any of SEQ ID NOS: 2 to 4. The peptide of the present invention consists of amino acid residues described in any one of SEQ ID NOS: 2 to 4. The peptide of the present invention is useful as an antigen for preparation of the antibody of the present invention.

According to a seventh aspect of the present invention, there is provided a method of preparing the antibody of the present invention, in which an antigen is a peptide having consecutive 8 to 30 amino acid residues selected from the amino acid sequence described in SEQ ID NO. 1. Preferable examples of the peptide used as the antigen include the peptide of the sixth aspect of the present invention and a peptide having consecutive 8 or more amino acids of the amino acid residues described in SEQ ID NO: 2. The "peptide having consecutive 8 or more and 16 or less amino acids of the amino acid residues described in SEQ ID NO: 2" means a peptide that contains any one of the following (1) to (9), which is a sequence on the upstream and/or downstream side followed after the sequence described below in SEQ ID NO: 2 and preferably consists of 10 or more, 12 or more, or 16 or more amino acids in total.

1) Arg Val Asp Ala Asp Ala Asp Pro (SEQ ID NO: 6)
2) Val Asp Ala Asp Ala Asp Pro Arg (SEQ ID NO: 7)
3) Asp Ala Asp Ala Asp Pro Arg Gln (SEQ ID NO: 8)
4) Ala Asp Ala Asp Pro Arg Gln Tyr (SEQ ID NO: 9)
5) Asp Ala Asp Pro Arg Gln Tyr Ala (SEQ ID NO: 10)
6) Ala Asp Pro Arg Gln Tyr Ala Asp (SEQ ID NO: 11)
7) Asp Pro Arg Gln Tyr Ala Asp Thr (SEQ ID NO: 12)
8) Pro Arg Gln Tyr Ala Asp Thr Val (SEQ ID NO: 13)
9) Arg Gln Tyr Ala Asp Thr Val Lys (SEQ ID NO: 14)

The details of the method of the present invention are as described in the section for the aspect of the antibody of the present invention.

The peptide of the present invention can be prepared by the method described in the section for the aspect of the antibody of the present invention.

EXAMPLES

Hereinafter, the present invention will be described more concretely by way of examples. However, the examples are only exemplary and the present invention should by no means be construed as being limited thereto. Further, symbols used in the following description are based on the symbols as a convention in the art.

Those manufactured by ProMedDx and Sera Care Life Science were purchased and used as sera of normal individuals and sera of patients suffering from sepsis used in the following examples.

Example 1

Preparation of Polyclonal Antibody Using Synthetic Peptide as Antigen 1-(1) Preparation of Peptide as Antigen <1>

To bind a peptide having the sequence described in SEQ ID NO: 2 (corresponding to a sequence at positions 53 to 68 described in SEQ ID NO: 5) (hereinafter, described as S68 peptide) to a carrier protein at the N-terminal thereof through an SH group, the peptide was synthesized by inserting cysteine into the N-terminal. That is, using a peptide synthesizer ABI433A (Applied), amino acid columns were aligned according to the amino acid sequence and an amino acid column for cysteine was placed on the N-terminal, followed by conducting automatic synthesis. The synthesized peptide was cut out from a resin by a conventional procedure and was then precipitated with ether, recovered, and dissolved in distilled water again, followed by freeze drying. After the resulting crude peptide had been dissolved, the peptide was eluted with a linear gradient of 5-70% acetonitrile concentration using a C18 reverse phase HPLC (CAPCELL-PAK, Shiseido Corp.), followed by collecting a fraction containing a target peptide. The collected fraction was freeze-dried and 2 to 3 mg of purified peptide was obtained.

1-(2) Preparation of Peptide Carrier Antigen Using Synthetic Peptide <1>

Each of two kinds of peptides prepared in 1-(1) was dissolved in distilled water to 10 mg/mL and the solution was mixed with 10 mg/mL of maleimide-activated keyhole limpet hemocyanin (Imject Maleimide Activated Mariculture Keyhole Limpet Hemocyanin (KLH) (PIERCE)) in equivalent amounts. After the mixture had been reacted for 2 hours at room temperature, the reaction mixture was desalted by an NAP-10 column (Amersham Bioscience) being equilibrated with physiological saline to obtain 1 mg of S68-peptide carrier antigen (hereinafter, described as S68 peptide-KLH). The concentration of proteins described in the following examples was obtained by dividing the amount of used KLH by the amount of liquid.

1-(3) Preparation of Peptide as Antigen <2>

Two kinds of peptide sequences represented in Table 1 were synthesized using a peptide synthesizer (PSSH-8, Shimadzu Corporation) by the same way as that of 1-(1) and purified, respectively. Each of the obtained peptides was about 5 mg in amount. By the way, the "number" in the table represents the name of a peptide explained below and the "position" represents the position thereof found in the amino acid sequence described in SEQ ID NO: 5.

TABLE 1

| Number | Position | Amino acid sequence | SEQ ID NO |
|---|---|---|---|
| P001 | 1-17 | Thr Thr Pro Glu Pro Cys Glu Leu Asp Asp Glu Asp Phe Arg Cys Val Cys | 3 |
| P002 | 14-32 | Arg Cys Val Cys Asn Phe Ser Glu Pro Gln Pro Asp Trp Ser Glu Ala Phe Gln Cys | 4 |

1-(4) Preparation of Peptide Carrier Antigen Using Synthetic Peptide <2>

Each of the peptides prepared in 1-(3) was dissolved in PBS (pH 7.2) containing 0.1 M EDTA, and as in the case of 1-(2) 3 mg of each of peptide carrier antigens where KLH bound to the respective peptides was obtained.

1-(5) Preparation of Polyclonal Antibody Using Synthetic Peptide <1>

For preparing a polyclonal antibody against S68 peptide-KLH prepared in 1-(2), a rabbit was immunized using S68 peptide-KLH. That is, 100 μg of each of S68 peptide-KLH was diluted with 500 μL of physiological saline and the solution was mixed with 500 μL of Freund's complete adjuvant (DIFCO) in equivalent amounts, followed by subcutaneously administering the mixture to the back of New Zealand white female rabbit (Kitayama Labes) weighing 2.1 to 2.2 kg. After 2 weeks, 100 μg of each of S68 peptide-KLH was diluted with 500 μL of physiological saline and the solution was mixed with 500 μL of Freund's incomplete adjuvant (DIFCO) in equivalent amounts, followed by subcutaneously administering the mixture to the back. After additional 2 weeks from that, 100 μg of S68 peptide-KLH was diluted with 1 mL of physiological saline and the solution was administered in an ear vein.

After 1 week from the completion of administration, blood was collected from the ear vein and antiserum was separated from the blood by routine procedures and an antibody was purified. First, ammonium sulfate was added to the antiserum up to a final saturation concentration of 33%. After the mixture had been stirred for 1 hour at 4° C., the separated precipitate was centrifuged. Then, the precipitate was dissolved in a 76-mM phosphate buffer (hereinafter, described as PBS (pH 6.4)) and the solution was dialyzed overnight. After the dialysate had been filtered, the filtrate was applied to a protein A column (Prosep-A, Millipore). Then, a binding IgG fraction was eluted with a 0.1 M glycine hydrochloride buffer (pH 3.0) to obtain a purified antibody. After dialysis with PBS (pH 6.4), the protein concentration was calculated from the absorbance at a wavelength of 280 nm (absorption coefficient: 0.533 mg/mL). Hereinafter, the obtained antibody will be described as an S68 peptide polyclonal antibody.

1-(6) Preparation of Polyclonal Antibody Using Synthetic Peptide as Antigen <2>

Using each of the peptide carrier antigens prepared in 1-(4), as in the case of 1-(3), the immunization and the purification of antiserum were performed to prepare each of peptide polyclonal antibodies (P001 and P002 polyclonal antibodies). Furthermore, the immunization was performed such that the peptide carrier antigen (0.5 mg/rabbit) was administered 5 times in two months. After the whole blood had been collected, each of the antisera (antiserum P001 and P002) was obtained.

1-(7) Preparation of Specific Purified Polyclonal Antibody

For purifying only an antibody against S68 peptide from the S68-peptide polyclonal antibodies, specific purification was performed by the following method. First, for biding the S68 peptide inserted with cysteine (hereinafter, described as C-S68 peptide) to a carrier through an SH group, 200 μg of C-S68 peptide was mixed per 1 mL of SufoLink Coupling Gel (PIERCE) and reacted according to the manual thereof. After the completion of the reaction, the remaining active group was blocked and then an S68 peptide-biding affinity column was prepared. Next, 7.92 mg of the purified IgG fraction described in 1-(3) was applied and then the column was washed with a phosphate buffer (pH 7.4) (Dulbecco, hereinafter, described as D-PBS (pH 7.4)), followed by eluting an anti-S68-peptide antibody with 0.1 M glycine hydrochloride buffer (pH 3.0). After the elution, pH was readjusted to neutral and then dialysis was performed with PBS, followed by calculating the protein concentration from an absorbance at 280 nm (absorption coefficient: 0.533 mg/mL). As a result, 0.52 mg of an anti-S68-peptide antibody (hereinafter, described as S68 antibody) was obtained.

Example 2

Preparation of Monoclonal Antibody Using Synthetic Peptide as Antigen

20 μg of S68 peptide-KLH prepared in Example 1-(2) was dissolved in 100 μL of physiological saline and mixed with an equivalent amount of Freund's complete adjuvant (DIFCO), followed by administering 100 μL of the mixture to each of the rear foot pads of a female Wister rat aged 8 weeks. After 2 weeks, the iliac lymph node was surgically excised and cell fusion was performed. The cell fusion was conducted according to Tamie Ando and Takeshi Chiba: "Introduction to Monoclonal Antibody Experimental Manipulation", page 83, 1991 (Kodansha). In other words, lymphocytes were separated from the lymph node using a cell strainer (Falcon) and mixed with myeloma cells (Sp2/O-Ag14) at a ratio of 5:1, followed by cell fusion using polyethylene glycol. Fused cells were suspended in an HAT medium and hybridomas were selected, followed by screening hybridomas producing the target antibody.

The screening was performed by an ELISA method in which sCD14(1-307)S286C was directly immobilized on a plate. That is, 50 μL of sCD14(1-307)S286C diluted with 0.1-M phosphate buffer (pH 7.4) to 1 μg/mL was added to each well of an immunoplate (Maxisorb, NUNC) and left to stand for 1 hour at 37° C. After that, the plate was washed with ion-exchanged water 5 times and then 100 μL of PBS (pH 6.4) containing 0.1% BSA was added to each well, followed by leaving the plate in standing for 1 hour at room temperature to effect blocking. Then, the culture supernatant sampled from the selected hybridomas was added to each well and allowed to react at 37° C. for 1 hour. After that, the plate was washed 3 times with physiological saline containing 0.05% Tween 20. Subsequently, 50 μL of a solution obtained by diluting peroxidase-labeled anti-rat immunoglobulin antibody (DAKO) with PBS containing 10% rabbit serum 1000-fold was added to each well. After reaction at 37° C. for 1 hour, the plate was washed 5 times in the same manner as above and a tetramethylbenzidine solution (TMB, BioFix) was added to each well. After a reaction for 10 minutes at room temperature, the reaction was stopped with a 0.5 M sulfuric acid solution and an absorbance at 450 nm was measured using a plate spectrophotometer (NJ-2100, Japan Intermed). As a result, a well containing hybridoma capable of producing an antibody binding to sCD14(1-307)S286C was selected.

Next, from the selected well, cloning was performed by a limiting dilution method according to Tamie Ando and Takeshi Chiba: "Introduction to Monoclonal Antibody Experimental Manipulation", page 83, 1991 (Kodansha). After 10 days, likewise, screening was performed using as an index the reactivity with sCD14(1-307)S286C and 6 kinds of hybridomas were selected. The selected hybridomas were cultivated in a 10% FCS/RPMI1640 medium (Sigma) and then cultivated in Hybridoma-SFM medium (Invitrogen) to produce an antibody. The antibody was purified using a protein G column (Prosep-G column, Millipore). The subtype of the purified F1146-17-2 antibody was determined to be rat IgG2b•κ by using a rat typing kit (ZYMED).

By the way, sCD14(1-307)S286C was prepared using the method described in Example 9 of WO 01/72993.

Example 3

Study of Assay System for Human Low-Molecular-Weight CD14

Using the antibodies described in Examples 1 and 2, the assay system for human low-molecular-weight CD14 with a sandwich EIA method was studied.

3-(1) Preparation of Recombinant Human CD14

First, for preparing a monoclonal antibody against sCD14 (1-285) to be used as a second antibody in the sandwich ELISA method, sCD14(1-285) as an immunogen was prepared in $E.$ $coli$. In order to express sCD14(1-285) in $E.$ $coli$, an expression plasmid pTrp1659 was constructed by the following method.

First, oligomer 8, links (5'-agc tta gga att t-3') (SEQ ID NO: 15) and oligomer 8, linkA (5'-cta gaa att cct a-3') (SEQ ID NO: 16) were synthesized.

Those oligomers were mixed in equivalent amounts and heated at 99° C. for 1 minute, and the mixture was then annealed by gradually cooling it down to room temperature. Furthermore, 5'-terminal thereof was phosphorylated by T4 Polynucleotide Kinase to prepare a linker.

Next, sense primer (5'-aca tct aga tga cca cgc cag aac ct-3') (SEQ ID NO: 17) and antisense primer (5'-ttt gga tcc tta cta gag atc gag cac tct-3') (SEQ ID NO: 18) were synthesized and PCR was performed using Pyrobest DNA Polymerase and plasmid pM1659 described in Example 8 of WO 01/72993 as a template.

After a reaction solution had been heated for 2 minutes at 90° C., the cycle of 98° C. for 10 seconds, 55° C. for 30 seconds, and 72° C. for 1 minute was repeated 30 times.

The resulting amplified product of about 900 bp was double-digested with XbaI and BamHI to collect DNA fragments. The vector pM710 described in Example 10 of JP 06-025289 A was double-digested with HindIII and BamHI and then subjected to agarose gel electrophoresis and collected. After three-ligation of the linker already phosphorylated, PCR-amplified DNA fragment/XbaI+BamHI digested fragment, and vector/HindIII+BamHI fragment, which were described above, the resultant was transformed into $E.$ $coli$ competent cells (JM109 (TOYOBO) to obtain a clone containing the target plasmid. Plasmid DNA was prepared by routine procedures.

Subsequently, JE7924 transformant strain for the production of sCD14(1-285) was prepared using an electroporation method.

First, $E.$ $coli$ JE7924 (J. Bacteriol 173, p. 4799, (1991)) was restored from a glycerol stock and incubated in an LB medium at 37° C. overnight. Furthermore, the bacteria were inoculated to 50 ml of a fresh LB medium and continuously incubated until the absorbance at 600 nm reached 0.5 to 0.6, followed by directly ice-cooling a culture flask for 30 minutes. Next, $E.$ $coli$ cells were collected and washed twice with ice-cooled sterilized distilled water and once with an ice-cooled 10% glycerol solution, followed by being suspended in 100 μL of an ice-cooled 10% glycerol solution. The suspension was dispensed into two tubes with 50 μL aliquots and quickly frozen in liquid nitrogen to prepare competent cells (JE7924), which were saved at −80° C. until the time of use.

Next, 50 μL of JE7924 competent cells was transformed with 30 ng of by electroporation device, Gene Pulser of BIO-RAD Co., Ltd. In addition, the settings at this time were a voltage of 2.5 kV and a resistance of 200Ω, and a capacitance of 25 μF. After that, the resultant was incubated in an LB agar plate containing 50 μg/mL of ampicillin overnight to obtain a clone transformed with pTrp1659. The clone thereof was incubated at 37° C. overnight in an LB medium and was then inoculated into a fresh medium, followed by being incubated for additional 5 hours. OD at 600 nm of culture suspension reached to 2 to 3, 3β-indole acrylic acid (Sigma CO., Ltd.) was added in a final concentration of 100 μg/mL and the mixture was incubated at 37° C. for 4 hours, resulting in induction expression of sCD14(1-285). Next, $E.$ $coli$ was collected and then an inclusion body was prepared using Bug Buster Protein Extraction Reagent (Novagen, Co., Ltd.). After that, the inclusion body was dissolved in an SDS-PAGE buffer and an SDS-PAGE was carried out to identify the expression of sCD14(1-285) by Western blotting by an anti-CD14 antibody.

Similarly, sCD14(1-285) to be used as an immunogen was prepared by incubating a JE7924 transformant strain in 1 L of an LB medium. First, the culture solution was centrifuged. After $E.$ $coli$ cells had been collected, the bacteria cells were washed with D-PBS and 50 mL of Bug Buster Protein Extraction Reagent (Novagen, hereinafter described as Bug Buster) was added to the collected bacteria cells. The bacterial cells were suspended and left standing for 30 minutes at room temperature. After lysing, the bacterial cells were subjected to a 10-minute sonication treatment (US-3, Iuchi Seieido) and centrifuged at 10000×g at 4° C. for 20 minutes to remove a supernatant. Likewise, an additional sonication treatment was performed on the cells and the resulting precipitate was suspended in 50 mL of Bug Buster. The suspension was added with 1 mL of a 10-mg/mL lysozyme (Seikagaku Corporation), and the whole was gently stirred and left standing for 10 minutes at room temperature. Subsequently, 200 mL of 1/10 volume of high-concentration Bug Buster was added to the mixture and the whole was stirred, followed by being subjected to centrifugation similarly to remove a supernatant. The resulting precipitate was suspended by the addition of 200 mL of 1/10 concentration of Bug buster and then the suspension was centrifuged similarly, followed by repeating such an operation several times. 100 mL of D-PBS was added in the finally obtained precipitate, resulting in an inclusion body.

For the preparation of sCD14(1-285), the inclusion body was dissolved in a TE buffer (pH 8.0, Nippon Gene) containing 1% Triton-X100 and the solution was then subjected to freeze and thawing 3 times, following by collecting a precipitate by centrifugation. The precipitate was dissolved in the TE buffer (pH 8.0, Nippon Gene) containing 1% Triton-X100 again, and the solution was ice-cooled and then subjected to a 12-minute ultrasonic treatment with 250 µA at intervals of 10 seconds and centrifuged, followed by collecting a precipitate. The precipitate was dissolved in a TE buffer (pH 8.0, Nippon Gene) containing 1% Triton-X100 and 0.2M NaOH, and then treated at 37° C. for 10 minutes, centrifuged, and re-dissolved three times, followed by collecting a precipitate. The resulting precipitate was dissolved in an aqueous solution containing 6 M guanidine hydrochloric acid to prepare purified sCD14(1-285). The concentration thereof was calculated by a protein assay of Bradford using BSA as a standard preparation.

3-(2) Preparation of Anti-CD14 Monoclonal Antibody

[1] Preparation of F1106-13-3 Antibody

Using sCD14(1-285) derived from *E. coli* described above as an antigen to be administered, a monoclonal antibody was prepared. First, 20 µg of purified sCD14(1-285) was mixed with Freund's complete adjuvant (DIFCO) in equivalent amounts, followed by intraabdominally administering 200 µL of the mixture to a 6-week-old female ddy mouse. After 2 weeks, 20 µg of purified sCD14(1-285) was mixed with Freund's incomplete adjuvant (DIFCO) in equivalent amounts, followed by intraabdominally administering 200 µL of the mixture. 50 µL of antigen was intraabdominally administered to the mouse 3 days before cell fusion. After 3 days, spleen was aseptically excised. Lymphocytes were isolated from the spleen and mixed with myeloma cells (P3x63-Ag. 8. U.1) in a ratio of 10:1 and fusion was performed with polyethylene glycol according to a method described on Tamie Ando and Takeshi Chiba: "Introduction to Monoclonal Antibody Experimental Manipulation", page 83, 1991 (Kodansha). After hybridomas had been selected using an HAT medium, screening of hybridomas producing antibodies biding to sCD14(1-285) was performed by an ELISA method.

First, sCD14(1-285) was diluted with PBS (pH 6.4) to 0.4 µg/mL and 50 µL of the resultant solution was then added to each well of an immunoplate (Maxisorb, NUNC) and reacted at 4° C. overnight. After that, the plate was washed with ion-exchanged water 5 times and then 100 µL of PBS (pH 6.4) containing 0.5% BSA was added to each well for blocking. Then, the sampled culture supernatant was added to each well and allowed to react at 37° C. for 1 hour. After that, the plate was washed 3 times with physiological saline containing 0.05% Tween 20. Subsequently, 50 µL of a solution obtained by diluting peroxidase-labeled anti-mouse immunoglobulin antibody (DAKO) with PBS containing 10% rabbit serum 1000-fold was added to each well. After a reaction at 37° C. for 1 hour, the plate was washed 5 times in the same manner as above and a tetramethylbenzidine solution (TMB, BioFix) was added to each well. After a reaction for 10 minutes at room temperature, the reaction was stopped with a 0.5 M sulfuric acid solution and an absorbance at 450 nm was measured using a plate spectrophotometer (NJ-2100, Japan Intermed). On the basis of the result, a well containing hybridoma producing an antibody binding to sCD14(1-285) was selected. Next, from the selected well, cloning was performed by a limiting dilution method according to Tamie Ando and Takeshi Chiba: "Introduction to Monoclonal Antibody Experimental Manipulation", page 83, 1991 (Kodansha). After 10 days, likewise, screening was performed using the reactivity with sCD14(1-285) as an index to select hybridomas. As a result, 12 types of hybridomas producing anti-sCD14(1-285) monoclonal antibody were selected.

The selected hybridomas were cultivated in a 10% FCS/RPMI1640 medium (Sigma) and then cultivated in Hybridoma-SFM medium (Invitrogen) to produce an antibody. The antibody was purified using a protein A column (Prosep-A, Millipore).

The subtype of F1106-13-3 antibody, which was an antibody having a particularly high sensitivity, was determined as IgG2b•κ using IsoStrip Mouse Monoclonal antibody Isotyping Kit (Roche).

[2] Preparation of F1031-8-3 Antibody

F1031-8-3 antibody was prepared using the method described in Example 7 of WO 01/22085. Briefly describing, 20 µg of CD14 protein derived from in human blood was dissolved in physiological saline and the solution was mixed with Freund's complete adjuvant (DIFCO) in equivalent amounts. Then, after 1 week from each of the initial intraabdominal administration and the second thereof 2 weeks after the initial, an increased level of antibody titer in serum was confirmed by an ELISA method on the reactivity with recombinant human CD14 protein as in the case of Example 5 of WO 01/22085. A 100-µg antigen was intraabdominally administered to a mouse as a final administration and after 3 days the spleen was surgically excised from the mouse. Lymphocytes were isolated from the spleen and mixed with myeloma cells (P3x63-Ag. 8. U.1) in a ratio of 10:1 and cell fusion was performed with polyethylene glycol. Hybridomas were selected using an HAT medium and after one week screening of hybridomas producing antibodies was performed by the ELISA method described above. The hybridoma that had reacted with the immobilized soluble CD14 protein was cloned by a limiting dilution method. After 10 days, similarly, screening was performed to obtain an anti-CD14 monoclonal antibody. F1031-8-3 antibody having the subtype of IgG2b•κ determined using IsoStrip Mouse Monoclonal antibody Isotyping Kit (Roche) was obtained as a typical antibody.

3-(3) Study of Assay System for Human Low-Molecular-Weight CD14

For preparing a system capable of specifically detecting human low-molecular-weight CD14, a sandwich EIA system was prepared using the antibodies described in Examples 1, 2, and 3-(2).

[1] Preparation of Peroxidase-Labeled Antibody

A peroxidase-labeled antibody was prepared according to the method of Nakane et al. (J. Histochem. Cytochem., vol. 22, p. 1084, 1974). That is, 4 mg of peroxidase (Toyobo) was dissolved in distilled water and the solution was then reacted at 25° C. for 20 minutes by the addition of 100 mM of periodic acid. After the completion of the reaction, 1.5% ethylene glycol was added to the reaction product and the whole was reacted at 25° C. for 10 minutes, followed by dialyzing against a 1-mm acetate buffer (pH 4.4). Each of the purified F1031-8-3 antibody and F1106-13-3 antibody was dialyzed with a 10-mM bicarbonate buffer (pH 9.5), and then 4 mg of peroxidase activated by the addition of 70 µL of a 0.2-M bicarbonate buffer (pH 9.5) per 4 mg was mixed with the antigen in equivalent amounts to allow a reaction at 25° C. for 2 hours. Next, 4 mg/mL of sodium borohydride was added and then the reaction was continued for additional 2 hours at 4° C. The reaction solution was dialyzed with PBS, resulting in a peroxidase-labeled F1031-8-3 antibody (hereinafter, it may be described as F1031-8-3-HRP) and peroxidase-labeled F1106-13-3 antibody (hereinafter, it may be described as F1106-13-3-HRP). The concentration of antibody was calculated from the amount of antibody used and the volume of the labeled antibody solution.

[2] Preparation of Sandwich EIA System <1>

Prepared was a 2-step sandwich EIA system using the S68 antibody prepared as an immobilized antibody in Example 1 and antibodies prepared in Example 3-(2)[1] and [2] as labeled antibodies. That is, S68 antibody was diluted with D-PBS (pH 7.4) to 10 μg/mL and 50 μL of the resultant solution was then added to each well of an immunoplate (Maxisorb, NUNC) and reacted at 4° C. overnight. After that, the plate was washed with ion-exchanged water 5 times and then 100 μL of D-PBS containing 0.1% StabilGuard (SurModics, Inc) and 0.1% Tween 20 was added to each well to effect blocking. Using as a diluent PBS (pH 7.4) containing 1% normal individual serum (serum from which soluble CD14 was removed using 3C10, hereinafter, described as CD14-absorbing serum) and 0.1% BSA, diluted specimens of human sera of normal individuals and human sera of patients suffering from sepsis were prepared by diluting the sera 20-fold, respectively. A diluted specimen was added in a concentration of 50 μL per well and reacted at 37° C. for 2 hours.

After the completion of the reaction, the specimen was washed three times with physiological saline containing 0.05% Tween 20 and 50 μL of F1031-8-3-HRP or F1106-13-3-HRP diluted to 0.6 μg/mL with 76 mM PBS (pH 8.0) containing 5% rat serum, 1% mouse serum and 0.1% Tween 20 was added to each well. After a reaction at 37° C. for 2 hours, the plate was washed 5 times in the same manner as above and a tetramethylbenzidine solution (TMB, BioFix) was added to each well. After a reaction for 20 minutes at room temperature, the reaction was stopped with a 0.5 M sulfuric acid solution and an absorbance at 450 nm was measured using a plate spectrophotometer (NJ-2100, Japan Intermed). As a result, as shown in Table 2, a soluble protein in blood, i.e., the low-molecular-weight CD14 being defined in the present invention, which could not increase in a normal individual but increase in a patient suffering from sepsis in the system in which antibody derived from S68 peptide was used, was able to be assayed.

[3] Preparation of Sandwich EIA System <2>

1) Prepared was a 2-step sandwich EIA system using the F1146-17-2 antibody prepared as an immobilized antibody in Example 2 antibody prepared in Example 3-(2) and [2] as a labeled antibody. F1146-17-2 antibody was diluted with PBS (pH 6.4) to 120 μg/mL and 50 μL of the resultant solution was then added to each well of an immunoplate (Maxisorb, NUNC) and reacted at 56° C. for 30 minutes. After that, the plate was washed with ion-exchanged water 5 times and then 100 μL of PBS containing 0.1% StabilGuard (SurModics, Inc) and 0.1% Tween 20 (Wako Pure Chemical Industries, Ltd.) was added to each well to effect blocking. Using as a diluent PBS (pH 6.4) containing 1% BSA, diluted specimens of human sera of normal individuals and human sera of patients suffering from sepsis were prepared by diluting the sera 10-fold, respectively. A diluted specimen was added in a concentration of 50 μL per well and reacted at 25° C. for 2 hours.

After the completion of the reaction, the plate was washed three times with physiological saline containing 0.05% Tween 20 and 50 μL of peroxidase-labeled F1031-8-3 antibody diluted to 0.5 μg/mL by 76 mM phosphate buffer (pH 8.0) containing 5% rat serum, 1% mouse serum, and 0.1% Tween 20 was added to each well. After a reaction at 25° C. for 2 hours, the plate was washed 5 times in the same manner as above and a tetramethylbenzidine solution (TMB, BioFix) was added to each well. After a reaction for 20 minutes at room temperature, the reaction was stopped with a 0.5 M sulfuric acid solution and an absorbance at 450 nm was measured using a plate spectrophotometer (NJ-2100, Japan Intermed). As a result, similarly to the S68 antibody, in the case of S68-peptide specific monoclonal antibody as shown in Table 2, low-molecular-weight CD14, which was almost not found in the sera of normal individuals but found in a high level in the sera of patients suffering from sepsis, was able to be assayed. That is, the result confirmed that an antibody that binds to S68 peptide can prepare a sandwich system irrespective of whether the antibody is polyclonal or monoclonal.

2) A two-step sandwich EIA system, where an immobilized antibody used was the polyclonal antibody prepared using the synthetic peptide as an antigen in Example 1-(6), was prepared. An assay was conducted using as specimens sera of human normal individuals and human patients suffering from sepsis by the same way as that of 3-[2], but P001 polyclonal antibody, P002 polyclonal antibody, or P012 polyclonal antibody was used in place of S68 antibody. As a result, as shown in Table 2, similarly to the S68 antibody, in the case of the polyclonal antibody using the synthetic peptide as an antigen, low-molecular-weight CD14, which was almost not found in the serum of a human normal individual but found in a high level in the serum of a patient suffering from sepsis, was able to be assayed. The results confirmed that a sandwich system can be performed even in a system using an antibody prepared using a peptide as an antigen, the peptide having 8 to 16 amino acid residues selected from the amino acid sequences at positions 1 to 285 of human high-molecular-weight CD14.

In Table 2, "++" represents a 4-fold or more absorbance at 450 nm compared with the absorbance of the diluent itself and "+" represents a 2-fold or more absorbance, and "−" represents an absorbance equal to the absorbance of the diluent.

TABLE 2

| Combination of antibodies | | Measured level | |
|---|---|---|---|
| Immobilizing side | Labeling side | Patient suffering from sepsis | Normal individual |
| S68 antibody | F1031-8-3 antibody | ++ | − |
| S68 antibody | F1106-13-3 antibody | ++ | − |
| F1146-17-2 antibody | F1031-8-3 antibody | + | − |
| P001 polyclonal antibody | F1031-8-3 antibody | + | − |
| P002 polyclonal antibody | F1031-8-3 antibody | + | − |

[4] Preparation of Sandwich EIA System <3>

A 3-step sandwich EIA system using F-1031-8-3 antibody as an immobilized antibody and S68 antibody as a labeled antibody was prepared. The present EIA system was performed by biotinylating the S68 antibody as follows. That is, 50 μL of D-Biotinoyl-ε-Aminocaproic Acid N-Hydroxysuccinimide Ester (Roche) prepared to 300 μg/mL by dissolving in DMSO was added to 0.5 mL of S68 antibody prepared to a concentration of 0.93 mg/mL by substituting with a 0.05-M phosphate buffer (pH 8.0) containing 0.15 M NaCl and the mixture was reacted while being stirred for 2 hours at room temperature. After the completion of the reaction, the reaction product was substituted with PBS (pH 7.4) by a desalting column (NAP-5, Amersham Bioscience). The concentration of the prepared biotinylated S68 antibody (hereinafter, it may be described as Bio-S68 antibody) was calculated using an absorption coefficient of 1.4 on the basis of absorbance at 280 nm.

The sandwich EIA system immobilized F1031-8-3 antibody on an immunoplate (NUNC) and blocked. A blocking solution was removed. Then, 500 ng/mL of sCD14(1-307) s286c (hereinafter, it may be described as a standard preparation) dissolved in 0.1% BSA/PBS and a solution with no standard preparation added were added to wells as negative control, respectively. The plate was washed after a reaction at 37° C. for 1 hour, and subsequently 50 μL of biotinylated S68 antibody prepared to 1 μg/mL by diluting with PBS (pH 7.4) containing 2% rat serum, 1% mouse serum, 1% rabbit serum, and 0.1% Tween 20 was added and reacted at 37° C. for 1 hour. After the completion of the reaction, the plate was washed and then a 10,000-fold diluted peroxidase-labeled streptavidin (which may be described as SA-HRP, Invitrogen) was added. The plate was washed after a reaction for 1 hour. After a color had been developed with a TMB solution (BioFix), the reaction was terminated by a terminating liquid and an absorbance at 450 nm was measured using a plate spectrophotometer E-Max (Molecular Device, Co., Ltd.).

As shown in Table 3, in the present system, a sandwich EIA system was able to be prepared. In other words, the inventors confirmed that a sandwich assay system can be prepared even if an antibody that binds to S68 peptide is used as an immobilized antibody or used as a free antibody or labeled antibody. In Table 3, "++" represents that the absorbance difference with 0 to 500 ng/mL of the standard preparation is 0.5 Abs or more, "+" represents 0.1 or more, and "−" represents less than 0.1.

[5] Preparation of Sandwich EIA System <4>

A 1-step EIA system was prepared such that immobilized and labeled antibodies were of the same system as that of [2], and a specimen and the labeled antibody were simultaneously added. That is, 25 μL of each of 0- and 500-ng/mL standard preparations was added to a S68-antibody-immobilized plate, followed by the addition of 25 μL of F1031-8-3-HRP prepared to 1 μg/mL by dilution with PBS (pH 7.4) containing 2% rat serum, 1% mouse serum, 1% rabbit serum, and 0.1% Tween 20. A reaction was carried out for 1 hour at 37° C. After the completion of the reaction, the plate was washed and colored by a TMB solution (BioFix). Then the reaction was terminated by a terminating liquid, followed by measuring an absorbance at 450 nm using a plate absorbance meter E-Max (Molecular Device, Co., Ltd.). As shown in Table 3, a sandwich EIA system was also made in the present system. That is, the inventors confirmed that a sandwich assay system using an antibody that binds to S68 peptide can conduct an assay without any relation to the reaction sequence.

[6] Preparation of Sandwich EIA System <5>

Immobilized and labeled antibodies were of the same system as that of [2], and a specimen and the labeled antibody were simultaneously reacted. Then, a 2-step EIA system to react with the immobilized antibody was prepared. That is, 25 μL of each of 0- and 500-ng/mL standard preparations was mixed with 25 μL of F1031-8-3-HRP prepared to 2 μg/mL with PBS (pH 7.4) containing 2% rat serum, 1% mouse serum, 1% rabbit serum, and 0.1% Tween 20. After the completion of the reaction, the reaction solution was added to an S68-antibody-immobilized plate, and the whole was reacted at 37° C. for 1 hour. The plate was washed and then colored by a TMB solution (BioFix) and then the reaction was terminated by a terminating liquid, followed by measuring an absorbance at 450 nm using a plate absorbance meter E-Max (Molecular Device, Co., Ltd.). As shown in Table 3, a sandwich EIA system was also made in the present system. That is, the inventors confirmed that a sandwich assay system using an antibody that binds to S68 peptide can conduct the assay without any relation to the reaction sequence.

[7] Preparation of Sandwich EIA System <6>

A sandwich EIA system using the specific biding of biotin-streptavidin was prepared.

1) Assay System Using Streptavidin on the Immobilizing Side

Streptavidin (PIERCE) diluted to 10 μg/mL with PBS (pH 7.4) was dispensed into immunoplates (NUNC) with 50 μL aliquots and immobilized by treating it at 4° C. overnight, respectively. After blocking, the liquid was discarded from them and 25 μL of each of biotinylated S68 antibodies prepared to 2 μg/mL with PBS (pH7.4) containing 2% rat serum, 1% mouse serum, 1% rabbit serum, and 0.1% Tween 20 and 0- and 500-ng/mL standard preparations dissolved in 0.1% BSA/PBS was added. After a reaction for 1 hour at 37° C., the plate was washed and subsequently 50 μL of F1031-8-3-HRP diluted to 1 μg/mL was added, followed by a reaction at 37° C. for 1 hour. After the completion of the reaction, the plate was washed and colored by a TMB solution (BioFix) and then the reaction was terminated by a terminating liquid, followed by measuring an absorbance at 450 nm using a plate spectrophotometer E-Max (Molecular Device, Co., Ltd.). The present systems were tested similarly even if the standard preparation, biotinated S68 antibody, and peroxidase-labeled F1031-8-3 antibody were simultaneously added. As shown in Table 3, sandwich EIA systems were able to prepared in both systems.

2) Assay System Using Peroxidase-labeled Streptavidin

The present system was prepared by the method shown in [4]. Furthermore, a 2-step method was studied, where a reaction was carried out at 37° C. for 1 hour after simultaneous addition of a standard preparation and biotinated F1031-8-3 antibody (which may be described as Bio-F1031-8-3) prepared according to [4] and about 10,000-fold diluted peroxidase-labeled streptavidin (Invitrogen) was added after washing. After the completion of the reaction, the plate was washed and colored by a TMB solution (BioFix) and then the reaction was terminated by a terminating liquid, followed by measuring an absorbance at 450 nm using a plate spectrophotometer E-Max (Molecular Device, Co., Ltd.). As shown in Table 3, in the present system, a sandwich EIA system was able be also prepared. That is, the inventors confirmed that the assay can be attained even if an immobilized or labeled substance is prepared using a second specific binding such as the biding of biotin and streptavidin as far as low-molecular-weight CD14 is sandwiched between an antibody that binds to S68 peptide and an antibody that binds to the assay analyte, low-molecular-weight CD14 in human serum. By the way, "Str" represents streptavidin and "Bio" represents biotinylating.

TABLE 3

| Example | Plate | Step 1 | Step 2 | Step 3 | Reactivity |
|---|---|---|---|---|---|
| [4] | F1031-8-3 antibody | Standard preparation | Bio-S68 antibody | SA-HRP | + |
| [5] | S68 antibody | Standard preparation F1031-8-3-HRP | — | — | ++ |
| [6] | S68 antibody | Standard preparation F1031-8-3-HRP | S68 antibody Plate | — | ++ |

TABLE 3-continued

| Example | Plate | Step 1 | Step 2 | Step 3 | Reactivity |
|---------|-------|--------|--------|--------|------------|
| [7] (1) | Str | Bio-S68 antibody Standard preparation | F1031-8-3-HRP | — | + |
| [7] (1) | Str | Bio-S68 antibody Standard preparation F1031-8-3-HRP | — | — | ++ |
| [7] (2) | S68 antibody | Standard preparation Bio-F1031-8-3 | SA-HRP | — | ++ |

Example 4

Preparation of Immunochromatographic Assay System 4-(1) Immunochromatographic Method Using Gold-colloid Labeled Antibody <1>

An assay system which could be easily used in a laboratory or by bedside was prepared. The outline of the assay system was shown in FIG. 1(A). First, a gold colloid-labeled F1106-13-3 antibody was prepared by mixing 1 mL of gold colloid (40 nm in particle diameter, B. B. International) with 9 µg of F1106-13-3 antibody. Next, a conjugate pad was prepared. That is, the gold colloid-labeled F1106-13-3 antibody was diluted with a conjugate-applying buffer so that an absorbance at 520 nm would be about 1.5 and 1 mL of the resultant solution was then applied on a 33-Glass strip of 10×150 nm, followed by drying under reduced pressure overnight. At this time, the antibody titer of gold colloid-labeled F1106-13-3 antibody in a reagent per test was about 50 units (1 unit equals 1 µL of gold colloid-labeled F1106-13-3 antibody at OD520=1.0). The antibody-immobilized membrane was prepared as follows. S68 antibody was diluted to 1 mg/mL with PBS (pH 7.4) and the solution was linearly applied on a nitrocellulose membrane (FF85/100, Schleicher & Schuell) in an amount of 0.75 µL/cm using an inkjet coating machine manufactured by BioDot Co., Ltd. At this time, a control line (anti-mouse polyclonal antibody, DAKO) was simultaneously applied. After drying, the membrane was immersed in a blocking liquid containing 0.5% casein for 30 minutes and then an excess part of the liquid was removed, followed by drying again. Next, an immunochromatographic reagent was formulated using each of the prepared materials. That is, a conjugate pad, immobilized membrane, an upper-absorbing pad (#900 filter paper, Schleicher & Schuell), or sample-dropping pad (33-Glass glass fiber filter, Schleicher & Schuell) was attached on a PB020 plastic-backing sheet (BioDot) and then cut in 5 mm in width by a strip cutter manufactured by BioDot Co., Ltd. The cut strip was housed in a housing case (NIPPN Technocluster, Inc.) and provided as an immunochromatographic reagent.

An assay was performed as described below using the prepared reagent. A standard preparation diluted $10^n$ folds within the range of 10,000 to 1 ng/mL with 1% BSA-PBS was provided as a sample. Then, 100 µL of the sample was dropped into the reagent to determine the presence or absence of a line after the mixture had been left to stand at room temperature for 20 minutes. The criteria for the judgment were as follows:

(++): Level at which a thick line is developed so that the line can be clearly judged as positive;

(+): Level at which color development can be judged as a line even though the color development is pale;

(±): Level at which what looks like color development is slightly observed but difficult to be recognized as a line; and (−): Level at which no color development is recognized.

Figure 2:
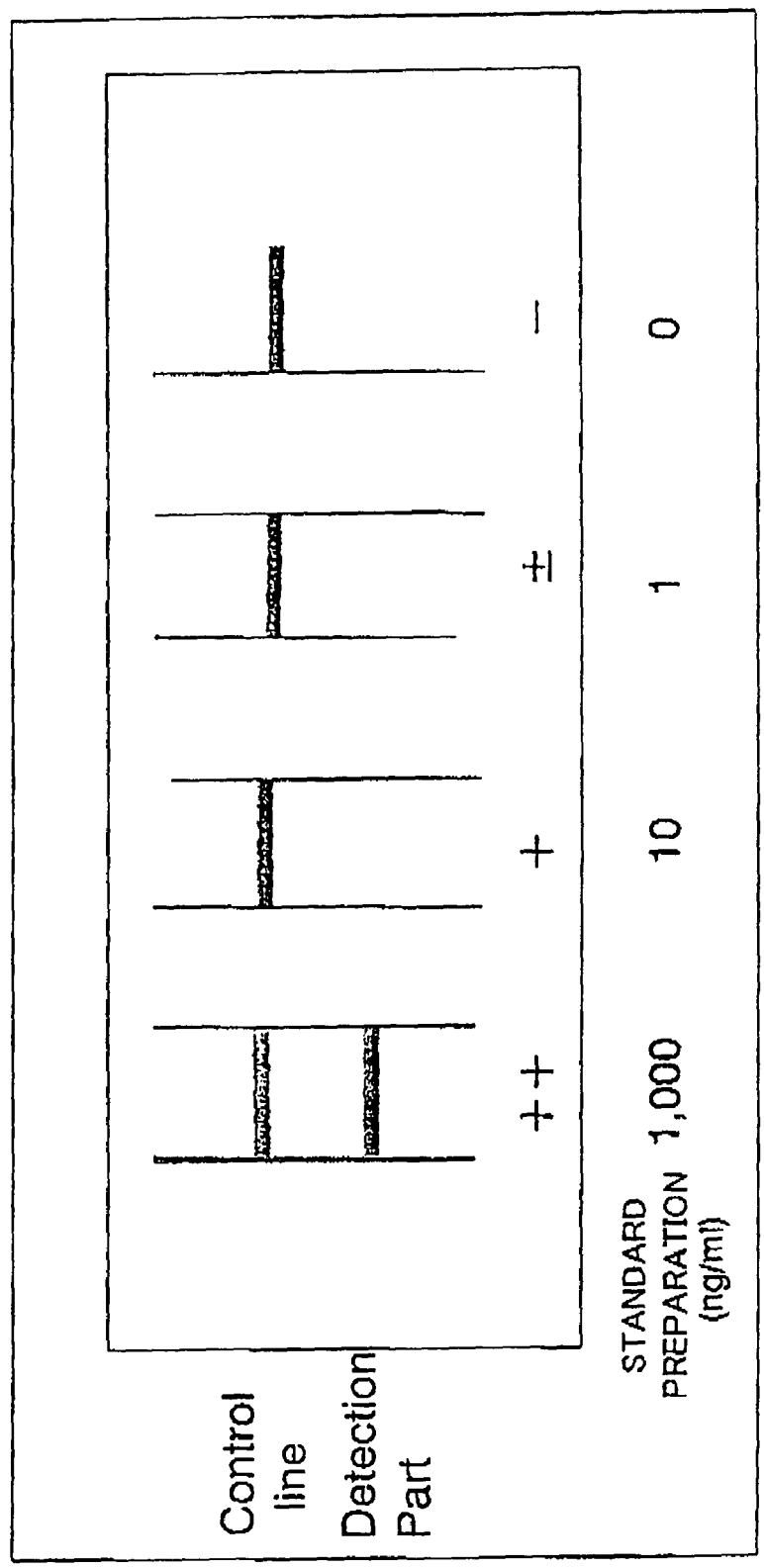
FIG. 2 shows the results of the assay performed on a standard substance by an immunochromatography kit using the S68-peptide polyclonal antibody.

As a result, as shown in FIG. 2 and Table 4, the sensitivity of "+" or more was obtained at a sample concentration of 10 ng/mL or more. Therefore, the result confirmed that the assay can be performed simply and quickly by an immunochromatographic system.

4-(2) Immunochromatographic Method Using Gold Colloid-labeled Antibody <2>

The assay was conducted while the immobilized antigen and gold colloid-labeled antibody of the immunochromatographic assay system prepared in 4-(1) were arranged inversely. The gold-colloid marker of S68 antibody and immunochromatographic system were able to be prepared by the same way as that of 4-(1). As a result, as shown in Table 4, the sensitivity of "+" or more was obtained at a sample concentration of 100 ng/mL or more.

TABLE 4

| Gold colloid-labeled | Immobilized | Sample concentration (ng/mL) | | | | | |
|---|---|---|---|---|---|---|---|
| | | 10000 | 1000 | 100 | 10 | 1 | 0 |
| F1106-13-3 | S68 | ++ | ++ | + | + | ± | − |
| S68 | F1106-13-3 | ++ | + | + | ± | ± | − |

4-(3) Preparation of Immunochromatographic Method Using Streptavidin-biotin System In addition, an immunochromatographic assay using a streptavidin-biotin system was prepared. The outline of the assay was shown in FIG. 1(B). First, according to Example 3-2[4], F1031-8-3 antibody was biotinated. Then, a gold colloid-labeled streptavidin was prepared by mixing 1 mL of gold colloid (40 nm in particle diameter, B. B. International) with 10 µg of streptavidin. The gold colloid-labeled streptavidin was diluted with a conjugate-applying buffer so that an absorbance at 520 nm would be about 1.5 and 1 mL of the resultant solution was then applied on a 33-Glass strip of 10×150 nm, followed by drying under reduced pressure overnight. At this time, the antibody titer of gold colloid-labeled streptavidin in a reagent per test was about 50 units (1 unit equals 1 µL of gold colloid-labeled streptavidin at OD520=1.0). The antibody-immobilized membrane was prepared as follows. S68 antibody was diluted to 1 mg/mL with PBS (pH 7.4) and the solution was linearly applied on a nitrocellulose membrane (FF85/100, Schleicher & Schuell) in an amount of 0.75 µL/cm using an inkjet coating machine manufactured by BioDot Co., Ltd. At this time, a control line (anti-mouse polyclonal antibody, DAKO) was simultaneously applied. After drying, the membrane was immersed in a blocking liquid containing 0.5% casein for 30 minutes and then an excess part of the liquid was removed, followed by drying again. Next, an immunochromatographic reagent was formulated using each of the prepared materials.

That is, a conjugate pad, immobilized membrane, an upper-absorbing pad (#900 filter, Schleicher & Schuell), or sample-dropping pad (33-Glass glass fiber filter, Schleicher & Schuell) was attached on a PB020 plastic-backing sheet (BioDot) and then cut in 5 mm in width by a strip cutter manufactured by BioDot Co., Ltd. The cut strip was housed in a housing case (NIPPN Technocluster, Inc.) and provided as an immunochromatographic reagent. An assay was performed as described below using the prepared reagent. A standard preparation diluted $10^n$ folds within the range of 10,000 to 1 ng/mL with 1% BSA-PBS was provided as a sample. Then, 100 μL of the sample was dropped into 100 μL of reagent containing 0.1 μg of biotinized F1031-8-3, and the whole was mixed. Then, 100 μL of the mixture was dropped into a sample-dropping pad of the housing case to determine the presence or absence of a line after the mixture had been left to stand at room temperature for 20 minutes. Therefore, in the present system, the sensitivity of "+" or more was also obtained at a concentration of 100 ng/mL or more just as in the case of (1).

Example 5

Preparation of Flow-through Assay System

A flow-through assay system is prepared according to JP 06-273419 A. That is, 1 g of a disperse dye (Red Violet, Kayaron, Co., Ltd.) is suspended in 10 mL of distilled water, and then resuspended in 5 mL of distilled water after being washed with distilled water. 0.2 mL of 0.5-mg/mL F1031-8-3 antibody diluted with physiological saline is added to 0.2 mL of the disperse dye and the whole is incubated at 45° C. for 30 minutes. After the resultant has been cooled on ice, centrifugal separation is performed. The resulting precipitate is resuspended in PBS (pH 7.4) containing 0.5% BSA and 10% lactose to prepare a disperse dye-labeled F1031-8-3 antibody. Next, the disperse dye-labeled F1031-8-3 antibody is dispensed with 0.1 mL aliquots and immersed into filter paper (No. 63, Advantec Toyo) cut into 14 mm in diameter, followed by freeze-drying to prepare a porous body adhered with a soluble reagent.

Immobilization on a membrane is performed as follows. First, 2 mg/mL of S68 antibody diluted with physiological saline is applied on a nitrocellulose membrane (Advantec Toyo) of 5 microns in pore diameter and dried at 37° C. Next, blocking is performed using PBS (pH 7.4) containing 1% BSA to prepare an antibody-immobilized membrane. The prepared materials are assembled in a housing case in the following order. An assay reagent is prepared by assembling the porous body adhered with a soluble reagent, antibody-immobilized membrane, polypropylene-laminated filter paper (No. 28, Advantec Toyo), and a transparent plate made of polycarbonate of 0.5 mm in thickness in order. An assay is initiated by the addition of 0.5 mL of a sample to the assay reagent and a judgment is performed by observing color from the back side by the naked eyes after the sample has been completely absorbed.

Example 6

Specificity of S68 Antibody

Figure 3:
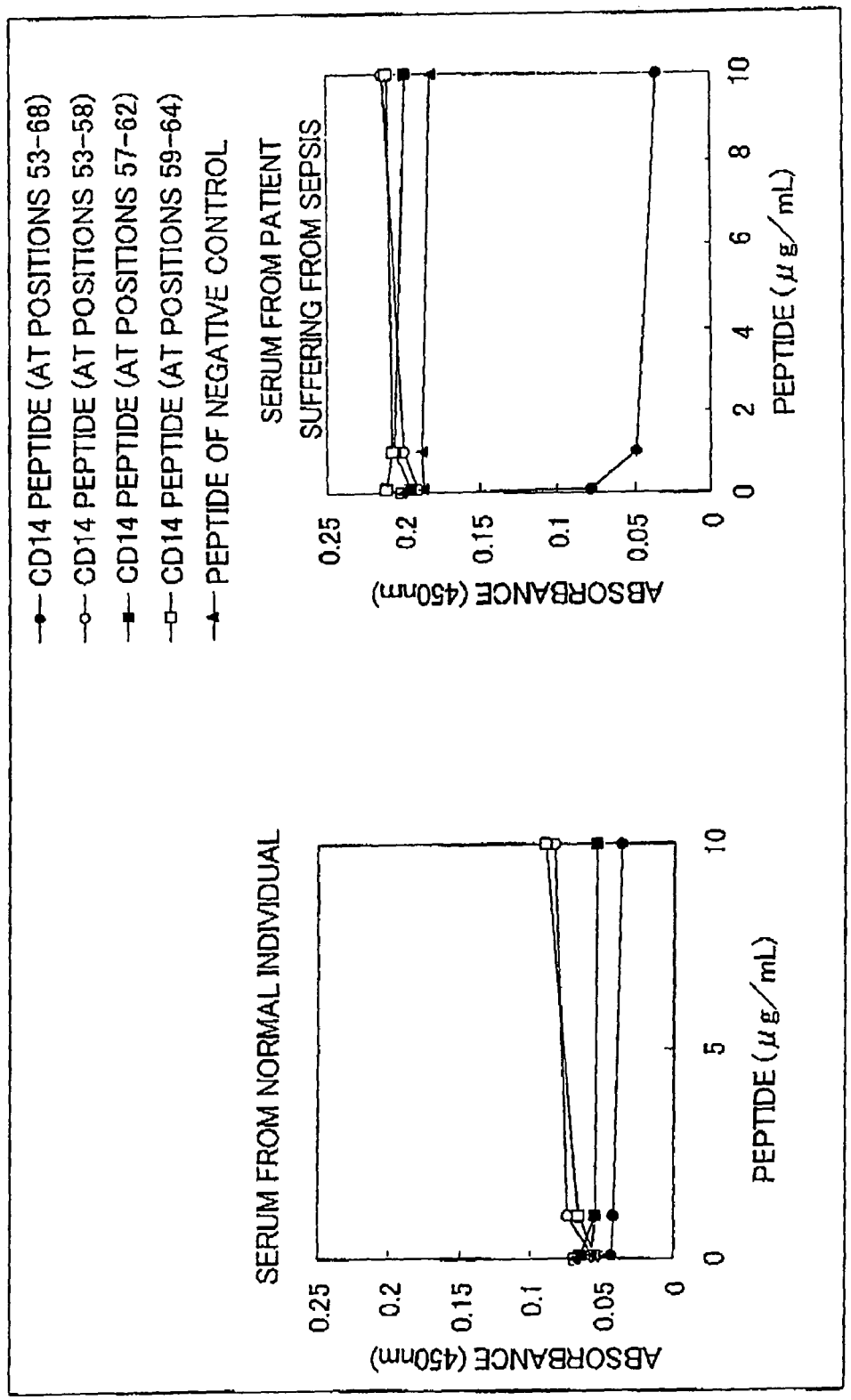
FIG. 3 shows the results in which only an S68 peptide inhibits the binding between the S68-peptide polyclonal antibody and a low-molecular-weight CD14 protein, in which part (A) shows a state where no binding is found in the sera of normal individuals and part (B) shows the inhibition of binding with the S68 peptide in the sera of patients suffering from sepsis.

For confirming the specificity of S68 antibody prepared in Example 1, the inventors studied whether blocking occurs by a peptide by the same assay as that of Example 3-(3). That is, S68 peptide (amino acid sequence at positions 53 to 68), synthetic polypeptide prepared by the same way as that of Example 1 (amino acid sequence at positions 53 to 58, amino acid sequence at positions 57 to 62, and amino acid sequence at positions 59 to 64), or negative control peptide (SEQ ID NO: 19) (Cys Glu Gly Asn Gly Asn Asn Phe Glu Ser Arg Glu Ala Cys) was diluted to 0, 0.1, 1, and 10 μg/mL and 25 μL of each diluted solution was added to 25 μL of each of 50-fold diluted solutions of the sera obtained from patients suffering from sepsis and the sera of normal individuals to initiate a competitive reaction by mixing with S68 antibody. After that, the levels of low-molecular-weight CD14 bound to S68 antibody without inhibition by any peptide were determined. As a result, as shown in FIG. 3, in both the sera of the normal individuals showing low levels and of patients suffering form sepsis showing high levels, the binding between S68 antibody and the low-molecular-weight protein in blood was inhibited in the case of S68 peptide but not inhibited in the case of other partial peptides (each containing 6 amino acids) and a negative control peptide. The above result confirmed that a protein being detected in blood by S68 antibody is specifically recognized by S68 antibody. In addition, the result also confirmed that the sequence recognized by the antibody requires a length of at least 7 amino acids because the inhibition can not be attained by three kinds of synthetic peptides (the number of amino acids: 6) corresponding to the partial peptides of S68 peptide.

Example 7

Reaction Rate Constant of Prepared Antibody

The specificities and reaction rate constants of S68 antibody prepared in Example 1 and F1146-17-2 antibody prepared in Example 2 were analyzed using Biacore 3000 (Biacore), respectively. First, S68 peptide-BSA to be immobilized was prepared by the same way as one described in Example 1 using maleimidated BSA (Imject Maleimed Activated BSA, PIERCE). Next, the S68 peptide-BSA was immobilized on a censor tip CM5 (Biacore) using an amine-coupling kit (Biacore). An assay was performed such that HBS-EP (Biacore) was used as a running buffer and a dilution series (50, 100, 150, 200, and 300 nM) of F1146-17-2 antibody was injected into flow cells. The data analysis was performed using Biaevaluation software version 3.0 (Biacore) by subtracting reference-cell data from flow-cell measurement data of S68 peptide-BSA. As a result of analyzing a dissociation constant (KD), the F1146-17-2 antibody showed affinity as high as $4.8 \times 10^{-9}$ M. By the way, the KD value of specifically-purified rabbit S68 peptide polyclonal antibody measured similarly was $2.2 \times 10^{-10}$ M.

Example 8

Specificity of Anti-CD14 Monoclonal Antibody 8-(1) Analysis of F1106-13-3 Antibody For clarifying a binding region (epitope) of F1106-13-3 antibody, a peptide library membrane (Custom SPOTs, Sigma Genosys) on which the amino acid sequence of CD14 was synthesized from the N-terminal thereof 10 amino acids at a time was used for analysis. That is, the membrane was blocked based on the instruction manual thereof and then was reacted with F1106-13-3 antibody, washed, and then reacted with β-galactosidase-bound anti-mouse antibody. After the membrane had been washed, a peptide sequence on which the antibody was bound was detected using X-gal. By the way, the peptide sequences on the peptide library membrane were analyzed using 19 peptides which were synthesized such that 10 amino acids were subjected to the synthesis at a time so as to overlap two amino acids of the respective C terminals of the sequences of amino acids at positions 1 to 154. The peptides were prepared by the same way as that of Example 1-(1).

The result found that F1106-13-3 antibody binds to the region corresponding to an amino acid sequence at positions 17 to 26 of SEQ ID NO: 5 (CNFSEPQPDW) from the N-terminal of high-molecular-weight CD14.

8-(2) Analysis of F1031-8-3 Antibody <1>

For confirming the specificity of F1031-8-3 antibody, using sCD14(1-285) derived from *E. coli* described in Example 3-(1) and sCD14(1-356) and sCD14(1-307)S286C prepared from COS cells using methods described in Examples 8 and 9 of WO 01/72993, the binding activity was determined.

First, sCD14(1-356), sCD14(1-307)S286C, sCD14(1-285), or BSA was immobilized 250 ng/spot on a membrane, Hybond-C extra (Amersham Bioscience), and after drying it was blocked by 0.05% Tween 20 containing 0.05 g/mL of skim milk (Meiji Milk Products), PBS (pH 6.4). After the resultant had been left to stand for 1 hour at room temperature, F1031-8-3 antibody diluted to 3 μg/mL with 0.05% Tween 20 containing 0.5% BSA, PBS (pH 6.4) was added and reacted for 1 hour at room temperature, followed by washing with 0.05% Tween 20, PBS (pH 6.4).

Next, peroxidase-labeled anti-mouse immunoglobulin antibody (DAKO) diluted 500 folds with 0.05% Tween 20 containing 10% rabbit serum, PBS (pH 6.4) was added and reacted for 30 minutes at 37° C. Then, the membrane was washed similarly, followed by confirming the binding activity of the antibody with ECL kit (Amersham Bioscience). As a result, as shown in Table 5, F1031-8-3 antibody bound to sCD14(1-285), sCD14(1-307)S286C, and sCD14(1-356) derived from *E. coli* not to BSA. Thus, the result found that the F1031-8-3 antibody specifically recognized all types of CD14 proteins. In Table 5, "+" represents a situation in which a spot was detected on a film and "−" represents a situation in which no spot was detected.

TABLE 5

|  | sCD14 (1-356) | sCD14 (1-307) S286C | sCD14 (1-285) | BSA |
|---|---|---|---|---|
| Binding activity | + | + | + | − |

8-(3) Analysis of F1031-8-3 Antibody <2>

For clarifying a binding region (epitope) of F1031-8-3 antibody, the spots analysis was performed as in the case of 8-(1). However, in the spots method, no recognition region of F1031-8-3 antibody could be specified. For the purpose of analyzing the similarity of the recognition regions of both antibodies, in the sandwich EIA system of Example 3-(3)[2] where S68 antibody was used as immobilized one and F1031-8-3-HRP was used as labeled one, an inhibition test was performed using F1106-1-3 antibody.

First, as in the case of Example 3-(3)[2], 100 ng/mL of the standard preparation was added to and reacted with an S68-antibody-immobilized plate. After the plate had been washed, before the addition of F1031-8-3-HRP, a 25-μL buffer containing 6 μg/mL of F1106-13-3 antibody, mouse IgG antibody, or no antibody was added. Then, 25 μL of F1031-8-3-HRP antibody was added, followed by the measurement by the same way as that of Example 3-(3)-[2].

As shown in Table 6, no inhibition occurred in the mouse IgG antibody addition system while the inhibition of binding between F1031-8-3 and standard preparation by F1106-13-3 antibody occurred. This fact indicated that F1106-13-3 antibody may bind to at least one region to be recognized by F1031-8-3 antibody. By the way, an "inhibition rate" was calculated from each absorbance being decreased at the time of defining the absorbance of the buffer alone as 100%.

TABLE 6

| Additive | Inhibition rate (%) |
|---|---|
| Mouse IgG antibody | 2 |
| F1106-13-3 antibody | 70 |

Example 8

Assay Kit for Human Low-molecular-CD14

8-(1) Typical Format of Assay Kit for Sandwich EIA System

A typical format of a soluble protein kit using a combination of immobilized and labeled antibodies that show high levels of human low-molecular-CD14 in the specimen patients suffering from sepsis and low levels in specimen from normal individuals in Example 3-(3) will be described below.

<1> Immobilized antibody: Plate on which S68 antibody is immobilized
<2> Labeled antibody: Peroxidase-labeled F1031-8-3 antibody
<3> Substrate solution (tetramethylbenzidine solution)
Other Accessories
Configuration Example of a Plate System
<4> Plate-washing solution (0.9% NaCl, 0.05% Tween 20 solution)
<5> Sample-diluting solution (0.1%-BSA-containing PBS solution)
<6> Reaction-terminating liquid (0.5 M $H_2SO_4$ solution)
<7> Standard preparation (CD14(1-307)S286C)
Measuring Instruments for Performing an Assay Using the Above Assay Kit <Example>
<8> Plate spectrophotometer (e.g., E-Max (Molecular Device, Co., Ltd.))

8-(2) to (11) Configuration Examples of Assay Kit for Sandwich EIA System

In addition to 8-(1), the examples of the assay kit for a sandwich EIA system are shown in Table 7. <1> represents a binding substance immobilized on a plate. <2> represents a labeled binding substance. The constituent elements of <3> to <7> and a measuring instrument <8> as a reference example are identical with 8-(1). <9> represents an antibody bound with a second specific biding substance.

TABLE 7

|  | <1> | <2> | <9> |
|---|---|---|---|
| (2) | F1146-17-2 antibody | F1031-8-3-HRP |  |
| (3) | S68antibody | F1106-13-3-HRP |  |
| (4) | F1146-17-2 antibody | F1106-13-3-HRP |  |
| (5) | F1031-8-3 antibody | S68 antibody-HRP |  |
| (6) | F1031-8-3 antibody | F1146-17-2-HRP |  |
| (7) | F1106-13-3 antibody | S68 antibody-HRP |  |
| (8) | F1106-13-3 antibody | F1146-17-2-HRP |  |
| (9) | F1031-8-3 antibody | SA-HRP | Bio-S68 antibody |
| (10) | Str | F1031-8-3-HRP | Bio-S68 antibody |
| (11) | S68 antibody | SA-HRP | Bio-F1031-8-3 |

8-(12) Standard Curve of Assay Kit for Sandwich EIA System

Figure 4:
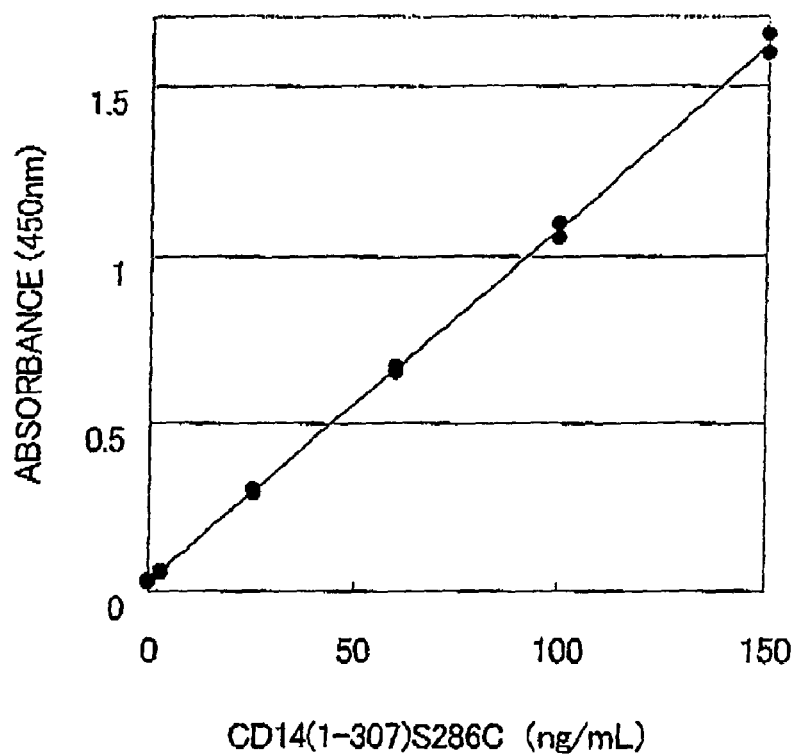
FIG. 4 is a diagram that represents a standard curve obtained by an EIA kit for low-molecular-weight CD14 of the present invention using an sCD14(1-307)S286C protein.
Figure 5:
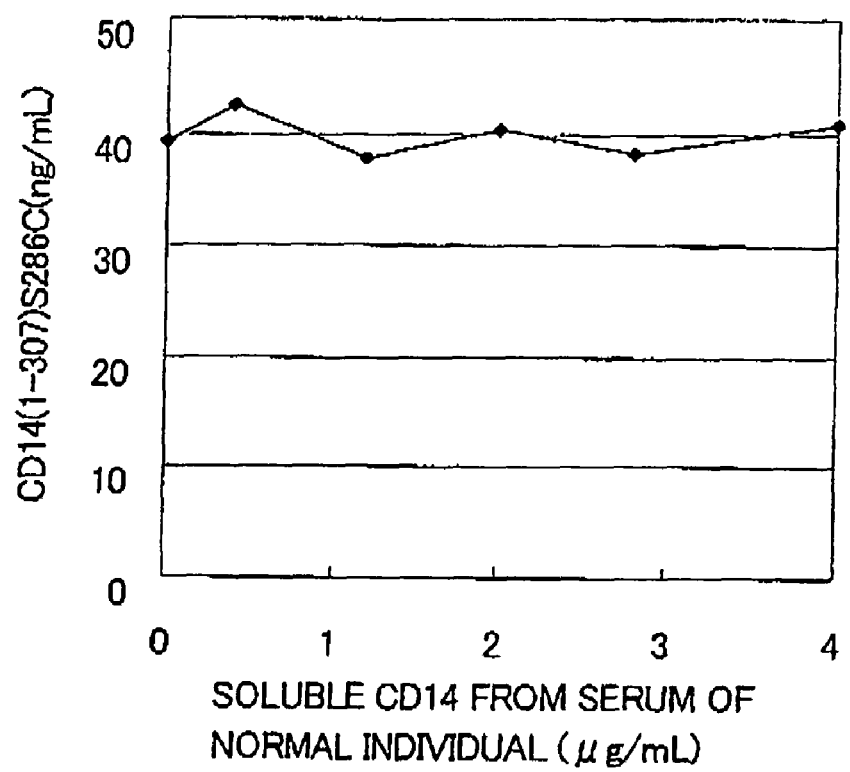
FIG. 5 is a diagram illustrating a case where a soluble CD14 protein derived from the serum of a normal individual does not affect the values measured by the EIA kit for low-molecular-weight CD14 of the present invention using the sCD14(1-307)S286C.

Using the assay kit of (1), an assay was performed by the same way as that of Example 3-(3)[2]. That is, S68 antibody was diluted to 10 μg/mL with D-PBS (pH 7.4) and 50 μL of the resultant solution was then added to each well of an immunoplate (Maxisorb, NUNC). After a reaction at 4° C. overnight, the plate was washed five times with ion-exchanged water and blocked by the addition of 100 μL of D-PBS containing 0.1% StabilGuard (SurModics, Inc.) and 0.1% Tween 20 to each well. Next, 76 mM PBS (pH 7.4) containing 1% CD14-absorbing serum and 0.1% BSA was used as a diluent to prepare a dilution series of 0, 3, 25, 60, 100, and 150 ng/mL of CD14(1-307)S286C protein standard preparation. The dilution series of the standard preparation was added in an amount of 50 μL per well and reacted for 2 hours at 37° C. After the completion of the reaction, the plate was washed three times with physiological saline containing 0.05% Tween 20. Then, 50 μL of diluted labeled antibodies prepared by diluting 5% rat serum, 1% mouse serum, and peroxidase-labeled F1031-8-3 antibody to 0.6 μg/mL with 76 mM PBS (pH 8.0) containing 0.1% Tween 20 were added to each well. After a reaction at 37° C. for 2 hours, the plate was washed five times in the same way as above and a tetramethylbenzidine solution (TMB, BioFix) was added to each well. After a reaction for 20 minutes at room temperature, the reaction was terminated by a 0.5 M sulfuric acid solution and an absorbance at 450 nm was measured using a plate spectrophotometer (NJ-2100, Japan Intermed). A standard curve prepared was shown in FIG. 4. A simple assay system with high sensitivity as a measuring sensitivity of 0.6 ng/mL (blank+3SD) was realized.

8-(13) Specificity of Sandwich EIA System

For studying the influence of high-molecular-weight CD14 present in human serum on the assay system prepared, soluble CD14 derived from normal individual serum at a concentration of 0 to 4 μg/mL was added to the standard preparation of CD14(1-307)S286C to conduct the same assay as that of (12). As a result, there was no influence on the measured level even though the concentration of the soluble CD14 derived from normal individual serum was 4 μg/mL. The result found that the cross-reactivity of the present sandwich EIA system with high-molecular-weight CD14 was 0.3% or less. In other words, the result confirmed that the present system does not detect human serum high-molecular-weight CD14 and is specific to a soluble protein showing a high level in serum of a patient suffering from sepsis.

8-(14) Evaluation on Assay Kit for Sandwich EIA System

Reproducibility of the assay results of the kit of (1) was evaluated. The coefficient of variation (CV) of within-run reproducibility using 3 samples of specimens as in the case of (12) was 5.8, 3.6, and 3.5% and reproducibility between measurements was 6.2, 5.2, and 5.1%, respectively. Thus good results were obtained, while no influence of an anticoagulant (heparin, citric acid, or EDTA) was observed. The results described above showed that the present kit has a sufficient ability for the assay of human low-molecular-weight CD14.

8-(15) Example of Immunochromatographic Assay Kit

<1> Labeled antibody: F1031-8-3 antibody labeled with gold colloid
<2> Conjugate pad: Glass fiber filter (33-Glass strip, manufactured by Schleicher & Schuell) on which <1> is applied
<3> Antibody-immobilized membrane: Nitrocellulose membrane (FF85/100, manufactured by Schleicher & schuell) blocked by 0.5% casein and having an immobilizing line of S68 antibody and a control line (an immobilizing line of anti-mouse polyclonal antibody) on the downstream of the immobilizing line.
<4> Sample-dropping pad: 33-Glass glass fiber filter (manufactured by Schleicher & Schuell)
<5> Absorbing pad (#900 filter paper (manufactured by Schleicher & Schuell)
<6> Sheet: PB020 plastic backing sheet (manufactured by BioDot); <2> to <5> are assembled on <6> such that a liquid dropped in <4> is allowed to flow through <2>, <3>, and <5> in this order.
<7> Housing case (OEM case available from NIPPN 1. Technocluster, Inc.)

By the way, the outlines of <1> to <5> are represented in FIG. 1(A).

8-(16) to (19) Example of Immunochromatographic Assay Kit

Table 8 shows, in addition to 8-(15), examples of an assay kit for a sandwich EIA system utilizing the second specific binding between binding of biotin and streptavidin, and examples of an assay kit for a sandwich EIA system utilizing the fragment of an antibody that binds to a peptide having 16 amino acid residues described in SEQ ID NO: 2. <1> represents a labeled binding substance. The constituent elements <2> to <7> are identical. As a substance to be applied on <3>, <3>-(i) represents a binding substance to be immobilized on an immobilized membrane and <3>-(ii) represents a binding substance to be immobilized on a control line. <8> represents an antibody bound with a second specific binding substance, the substance being a reagent to be applied on <2> or <4> as in the case of <1>, or to be added to a specimen or simultaneously added together with the specimen.

By the way, the outlines of (16) <1> to <5> are shown in FIG. 1(B), and (17) to (20) are similarly understood.

TABLE 8

| | <1> | <3>-(i) | <3>-(ii) | <8> |
|---|---|---|---|---|
| (16) | Gold colloid-labeled Str | S68 antibody | Anti-mouse polyclonal antibody | Bio-F1031-8-3 antibody |
| (17) | Gold colloid-labeled Bio | S68 antibody | Str | Str-F1031-8-3 antibody |
| (18) | Gold colloid-labeled F1031-8-3 antibody | Str | Anti-mouse polyclonal antibody | Bio-S68 antibody |
| (19) | Gold colloid-labeled S68 antibody | Str | Anti-rabbit polyclonal antibody | Bio-F1031-8-3 antibody |
| (20) | F(ab')$_2$ of gold colloid-labeled S68 antibody | F1103-13-3 antibody | Anti-rabbit polyclonal antibody | |

By the way, F(ab')$_2$ of S68 antibody labeled with gold colloid of (20) <1> is prepared as follows. The preparation of F(ab')$_2$ from S68 antibody is performed as follows using Immobilized Pepsin (PIERCE). That is, S68 antibody is dissolved in a 20 mM acetate buffer (pH 4.5) to be prepared to 5 mg/mL. 0.25 mL of Immobilized Pepsin is prepared by suspension according to the protocol of PIERCE and mixed with 1 mL of the above antibody. Next, the mixture is stirred for 4 hours in an incubator at 37° C., and then the reaction is terminated by the addition of 1.5 mL of 10 mM Tris-HCl (pH 7.5). The reaction solution is centrifuged (1000×g) to separate a gel and a supernatant. Then, the separated supernatant is added to 1 mL of prosep-A (Millipore) to allow the binding of peptides including Fc portion such as Fc fragment and undigested. Likewise, the mixture is centrifuged to collect the supernatant, and then the supernatant is dialyzed against PBS (pH6.4). The absorbance of F(ab')$_2$ at 280 nm is measured and then the concentration of F(ab')$_2$ is calculated from the absorption constant (0.533 mg/mL/cm$^{-1}$). The resulting F(ab')$_2$ is labeled with gold colloid as in the case of Example 4, resulting in F(ab')$_2$ of the gold colloid-labeled S68 antibody.

8-(21) Configuration Example of Flow-Through System

<1> Dye-labeled antibody: RED VIOLET dye-labeled S68 antibody

<2> Conjugate pad: Filter paper (No. 63, manufactured by Advantec Toyo Co., Ltd.) impregnated with the above (1)

<3> Antibody-immobilized membrane: Nitrocellulose membrane (Advantec Toyo) on which S68 antibody is immobilized <4> Absorbing pad: Filter paper (No. 28, Advantec Tokyo) laminated with polypropylene <5> Housing case: Case described in JP 06-273419 A (manufactured by Mochida Pharmaceutical); <2> to <4> are assembled in <5> such that a liquid dropped in <2> is allowed to flow through <2>, <3>, and <4> in this order.

Example 9

Detection of Human Low-molecular-weight CD14

(1) Gel Filtration Chromatography <1>

For analyzing the substance in serum of a patient suffering from sepsis detected by the assay kit described in Example 8-(1), the serum of the patient suffering from sepsis was fractionated through a gel filtration chromatography column Superdex 200PC 3.2/30 (Amersham Bioscience) with SMART SYSTEM (Amersham Bioscience) using D-PBS as a elution buffer. Then, each fraction was assayed using the assay kit described in Example 8-(1) and the commercially available CD14-EIA kit (IBL-Hamburg). The molecular weight thereof was calculated by calibrating the column using aldolase (158 kDa), BSA (67 kDa), ovalbumin (43 kDa), and chymotrypsin (25 kDa) from the LMW calibration kit and HMW calibration kit (Amersham Bioscience).

Figure 6:
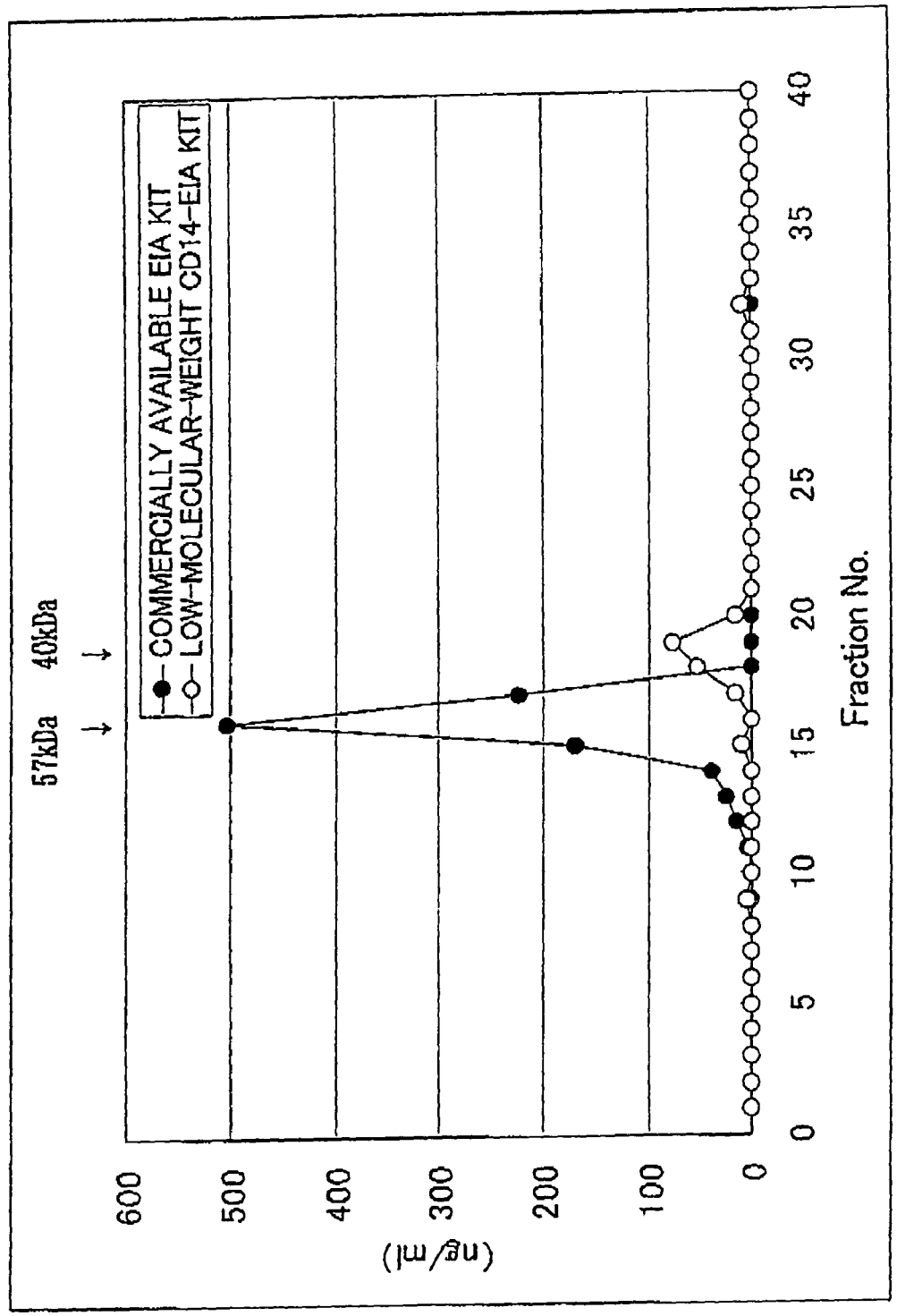
FIG. 6 is a diagram showing the results obtained by analyzing the low-molecular-weight CD14 protein and the high-molecular-weight CD14 protein in the sera of patients suffering from sepsis by using the EIA kit for low-molecular-weight CD14 and the commercially-available CD14-EIA kit (IBL-Hamburg), respectively, with gel filtration chromatography.

As a result, as shown in FIG. 6, the commercially available CD14-EIA kit detected soluble CD14 having a molecular weight of about 57 kDa, which was defined as high-molecular-weight soluble CD14 of 49 to 55 kDa conventionally reported. On the other hand, in the kit described in Example 8-(1), a peak derived from human low-molecular-weight CD14 detected in a patient suffering from sepsis was detected around a molecular weight of 35 to 45 kDa but no peak was detected around 57 kDa. Thus, the result confirmed that the kit described in Example 8-(1) specifically detects only a soluble protein present in blood.

(2) Gel Filtration Chromatography <2>

As in the case of (2)-<1>, 50 µl of serum from a patient suffering from sepsis was fractionated through a gel filtration chromatography column Superdex 75 10/300 GL (Amersham Bioscience) using 200 mM ammonium acetate (pH 6.8) as a elution buffer and was subjected to the assay using each kit. The molecular weight thereof was calculated by calibrating the column using BSA (67 kDa), ovalbumin (43 kDa), chymotrypsinogen (25 kDa), and ribonuclease A (13.7 kDa) from the LMW calibration kit and HMW calibration kit (Amersham Bioscience).

The results are shown in FIG. 7. In the kit described in Example 8-(1), a peak derived from human low-molecular-weight CD14 was detected around a molecular weight of 25 to 35 kDa.

(3) F1025-3-1 Antibody Affinity Column Chromatography

When a peaked fraction (e.g., fraction 12) derived from human low-molecular-weight CD14 obtained in (2)-<2> is applied to F1025-3-1 antibody affinity column chromatography, a peak derived from human low-molecular-weight CD14 is eluted in an affinity column non-absorbing fraction. By the way, the adjustment and operation of the F1025-3-1 antibody affinity column can be performed on the basis of the method described in Example 10 of WO 01/22085.

These results show that the human low-molecular-weight CD 14 is a soluble protein in blood that specifically binds to antibodies against a specific peptide described in SEQ ID NO: 2 having a sequence detected only in human CD14 and also binds to an anti-CD14 antibody recognizing an amino acid sequence at positions 17 to 26 from the N-terminal of human CD14. The gel filtration determines the molecular weight thereof to be 25 to 45 kD. Thus, it can be defined that the human low-molecular-weight CD 14 is smaller in molecular weight than high molecular-weight CD14 (the conventional native CD14). In addition, the low-molecular-weight CD14 does not bind to F1025-3-1 antibody that specifically binds to high-molecular-weight CD14.

Example 10

Assay of Low-molecular-weight CD14 in Sera of Patients Suffering from Various Kinds of Diseases 10 examples, from which isolates were identified, were used (Table 9) as the sera of patients suffering from sepsis. In addition, the assay was conducted using the assay kit described in Example 8-(1) on 52 examples of normal individuals (male 31 examples and female 21 examples), and patients suffering from various kinds of diseases (20 diseases, 60 examples).

TABLE 9

| Number | Sex | Age | Bacteria |
|---|---|---|---|
| 1 | Male | 41 | Coagulase-negative bacteria |
| 2 | Female | 44 | Coagulase-negative bacteria |
| 3 | Female | 61 | Faecium bacteria |
| 4 | Male | 52 | Serratia bacteria |
| 5 | Male | 37 | Escherichia coli |
| 6 | Female | 67 | Escherichia coli |
| 7 | Male | 70 | Staphylococcus aureus |
| 8 | Male | 51 | Pantoea agglomerans |
| 9 | Female | 81 | Escherichia coli |
| 10 | Male | 77 | Escherichia coli |

The level of low-molecular-weight CD14 in serum of a normal individual was in the range of 0.008 to 0.100 µg/mL and the average thereof was 0.04 µg/mL. In the case of a patient suffering from sepsis, the level of low-molecular-weight CD14 was in the range of 0.190 to 7.260 µg/mL and the average thereof was 2.0 µg/mL. The level of low-molecular-weight CD14 of the patient suffering from sepsis was higher than those of the normal individuals and patients suffering from other various kinds of diseases. Among patients suffering from other various kinds of diseases, there was no patient showing a high level, compared with that of the normal individual.

Example 11

Comparison with Commercially Available ELISA Kit for CD14 Soluble in Blood 11-(1) Assay of Soluble CD14 in Blood of Patients Suffering from Various Kinds of Diseases Specimens of Example 10 were assayed using the commercially available CD14-ELISA kit (IBL-Hamburg). The level of soluble CD14 in blood (estimated as a total of low-molecular-weight CD14 and high-molecular-weight CD14) of a normal individual was in the range of 5.6 to 11.2 µg/mL but an example of a high level in the case of a patient suffering from sepsis was observed. However, many cases that showed high levels of soluble CD14 were found in sera of patients suffering from various kinds of disease, so that there was no difference with the patients suffering from sepsis.

11-(2) Comparison with Kit Using S68 Antibody

The comparison with and investigation of the measured levels of low-molecular-weight CD14 determined in Example 11 were performed. As shown in Table 10, the commercially available CD14-EIA kit showed an almost 1.7-fold difference at maximum among the normal, various diseases, and sepsis, while the assay kit of Example 9-(1) showed a 50-fold difference between the normal individuals and the sepsis in spite of no difference between the normal individuals and various diseases. Therefore, the result was cleared that the measured level of the assay kit of Example 9-(1) specifically increases in sepsis.

TABLE 10

| | CD14 level in blood (µg/mL) | | | |
|---|---|---|---|---|
| | Normal | Various kinds of diseases | Sepsis | Ratio Sepsis/Normal |
| Assay kit of Example 9-(1) | 0.04 | 0.06 | 2.0 | 50.0 |
| Commercially available CD14-EIA | 7.6 | 9.0 | 13.2 | 1.7 |

The average level+3 S.D of the tested normal individuals was provided as a cut-off level (low-molecular-weight CD14-EIA: 0.134 µg/mL, commercially available CD14-EIA: 11.14 µg/mL) and then the analyses were divided into positive samples (sepsis) and negative samples (normal+various diseases). The results were shown in Table 11. According to the results, a rate of identical between both kits ((the number of identical for EIA positive+the number of identical for EIA negative)/total×100), sensitivity (the number of identical for EIA positive/positive examples×100), and specificity (the number of identical for EIA positive/negative examples×100) were calculated. As a result, as shown in Table 12, in the case of low-molecular-weight CD14-EIA, the identical rate was 94.3%, the sensitivity was 100.0%, and the specificity was 93.8%. Thus, it was found that the low-molecular-weight CD14-EIA could be useful in differential diagnosis on sepsis by defining the cut-off level. On the other hand, in the case of the commercially available CD14-EIA, there was no sensitivity and specificity which were specific to allow diagnosis of sepsis.

TABLE 11

| | Classification | | | |
|---|---|---|---|---|
| | Positive sample | Negative sample | | |
| | Disease | | | |
| | Sepsis | Normal | Various kinds of diseases | Total |
| Assay kit of Example 9-(1) | 10 | 51 | 54 | 115 |
| Commercially available CD14-EIA | 6 | 51 | 45 | 102 |
| Total | 10 | 52 | 60 | 122 |

TABLE 12

| | Assay kit of Example 9 | Commercially available CD14-EIA |
|---|---|---|
| Rate of identity (%) | 94.3% | 83.6% |
| Sensitivity (%) | 100.0% | 60.0% |
| Specificity (%) | 93.8% | 85.7% |

INDUSTRIAL APPLICABILITY

According to the present invention, there is provided the antibody prepared using a peptide as an antigen, the peptide having 8 to 30 amino acid residues selected from an amino acid sequence at positions 1 to 68 of human high-molecular-weight CD14, and also provided the antibody that binds to a peptide having amino acid residues described in SEQ ID NOS: 2 to 4.

Those antibodies can be used in an assay kit for human low-molecular-weight CD14 and the kit is able to quantitatively or qualitatively determine human low-molecular-weight CD14 with high sensitivity in a simple manner, so that the kit is useful for the diagnosis of a patient suffering from sepsis. In the present invention, the assay kit for human low-molecular-weight CD14 containing the above antibody and the assay method are provided. Furthermore, the novel diagnostic method for sepsis in which human low-molecular-weight CD14 is directly assayed is provided. Furthermore, the peptide useful in the preparation of the above antibody and the method of preparing the above antibody are provided.

The invention claimed is:

1. A sandwich immunoassay kit which detects human low-molecular weight CD14 without detecting human high-molecular weight CD14, comprising;
   (a) an antibody that binds to a peptide consisting of the amino acid sequence of SEQ ID NO:2, wherein said antibody binds to human low molecular weight CD14, but does not bind to human high molecular weight CD14; and
   (b) an antibody that binds to a peptide consisting of the amino acid sequence from the position of 17th to the position of 26th of SEQ ID NO:5;

wherein said human low-molecular weight CD14 has the characteristic features as follows;
   (1) no binding to F1025-3-1 (Accession No. FERM BP-7296) antibody,
   (2) showing a peak of elution in a molecular weight range of 25 to 45 kDa on a gel filtration chromatography, and
   (3) being obtainable from human blood.

2. A sandwich immunoassay kit which detects human low-molecular weight CD14 without detecting human high-molecular weight CD14, comprising;
   (a) an antibody that binds to a peptide consisting of the amino acid sequence of SEQ ID NO:2, wherein said antibody binds to human low molecular weight CD14, but does not bind to human high molecular weight CD14; and
   (b) an antibody that competes with an antibody which binds to a peptide consisting of the amino acid sequence from the position of 17th to the position of 26th of SEQ ID NO:5;

wherein said human low-molecular weight CD14 has the characteristic features as follows;
   (1) no binding to F1025-3-1 (Accession No. FERM BP-7296) antibody,
   (2) showing a peak elusion in a molecular weight range of 25 to 45 kDa on a gel filtration chromatography, and
   (3) being obtainable from human blood.

3. A monoclonal antibody that binds to a peptide consisting of the amino acid sequence from the position of 17th to the position of 26th of SEQ ID NO:5.

4. An isolated antibody that binds to human low-molecular weight CD 14, wherein the antibody is prepared by using a peptide consisting of the amino acid sequence of SEQ ID NO:2 as an antigen wherein said human low-molecular weight CD14 has the characteristic feature as follows:
  (1) no binding to the F1025-3-1 (Accession No. FERM BP-7296) antibody,
  (2) showing a peak in a molecular weight range of 25 to 45 kDa on a gel filtration chromatography, and
  (3) being obtainable from human blood,
  wherein said antibody does not bind to human high molecular weight CD14.

5. The antibody according to claim 4, wherein the antibody is a monoclonal antibody.

* * * * *